(12) United States Patent
Ryu et al.

(10) Patent No.: US 10,030,256 B2
(45) Date of Patent: Jul. 24, 2018

(54) **METHOD FOR PRODUCING LYSOPHOSPHATIDYLETHANOLAMINE 18:1 FROM MICROORGANISM OF *PSEUDOMONAS* SP**

(71) Applicant: KOREA RESEARCH INSTITUTE OF BIOSCIENCE AND BIOTECHNOLOGY, Daejeon (KR)

(72) Inventors: Beung Tae Ryu, Daejeon (KR); Young Pyo Lee, Daejeon (KR); Ji Hye Jung, Daejeon (KR); Sung Hee Jung, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/852,864

(22) Filed: Dec. 22, 2017

(65) Prior Publication Data

US 2018/0105849 A1  Apr. 19, 2018

Related U.S. Application Data

(63) Continuation-in-part of application No. PCT/KR2015/013227, filed on Dec. 4, 2015.

(30) Foreign Application Priority Data

Jun. 23, 2015 (KR) .......................... 10-2015-0089016

(51) Int. Cl.
  *C12P 7/64* (2006.01)
  *C12P 13/00* (2006.01)
  *C07F 9/10* (2006.01)

(52) U.S. Cl.
  CPC ............ *C12P 13/001* (2013.01); *C07F 9/103* (2013.01); *C12Y 301/01004* (2013.01)

(58) Field of Classification Search
  CPC ........... C12P 19/44; C12P 7/18; C12P 7/6445; C12P 7/6481; C12P 7/64
  See application file for complete search history.

(56) References Cited

U.S. PATENT DOCUMENTS

| | | |
|---|---|---|
| 5,110,341 A | 5/1992 | Palta et al. |
| 5,126,155 A | 6/1992 | Palta et al. |
| 6,426,105 B1 | 7/2002 | Palta et al. |
| 6,559,099 B1 | 5/2003 | Farag et al. |

FOREIGN PATENT DOCUMENTS

| | | |
|---|---|---|
| KR | 10-1997-0001484 B1 | 1/1997 |
| KR | 10-2001-0048900 A | 6/2001 |
| KR | 10-2002-0086604 A | 11/2002 |
| KR | 10-2003-0084200 A | 11/2003 |
| KR | 10-2013-0005770 A | 1/2013 |
| WO | WO2011046812 A1 | 4/2011 |

OTHER PUBLICATIONS

International Search Report for PCT/KR2015/013227.
Cowan, A. Keith, "Plant growth promotion by 18:0-lysophosphatidylethanolamine involves senescence delay", Plant Signaling & Behavior, vol. 4, No. 4, pp. 324-327, 2009.
Hong, Sung Myun et al., "Identification and testing of superior reference genes for a starting pool of transcript normalization in *Arabidopsis*", Plant & Cell Physiology, 51:1694-1706, 2010.
Jung, Jihye et al., "Translocation of phospholipase A2α to apoplasts is modulated by developmental stages and bacterial infection in *Arabidopsis*", Frontiers in Plant Science, vol. 3: Article 126, 2012.
Richard A.Jefferson et al., "GUS fusions: beta-glucuronidase as a sensitive and versatile gene fusion marker in higher plants", The EMBO Journal, vol. 6: pp. 3901-3907, 1987.
Ryu, SB et al., "Activation of phospholipase D and the possible mechanism of activation in wound-induced lipid hydrolysis in castor bean leaves", Biochem Biophys Acta. 1303:243-250 (Abstract), 1996.
Ryu, SB et al., "Characterization of a cDNA encoding *Arabidopsis* secretory phospholipase A2-alpha, an enzyme that generates bioactive lysophospholipids and free fatty acids", Biochem Biophys Acta.,1736:144-151 (Abstract), 2005.
Bowling, Scott A. et al., "A Mutation in *Arabidopsis* That Leads to Constitutive Expression of Systemic Acquired Resistance", The Plant Cell, vol. 6:1845-1857, 1994.
Heck, Silvia et al., "Genetic evidence that expression of NahG modifies defence pathways independent of salicylic acid biosynthesis in the *Arabidopsis-Pseudomonas syringae* pv. tomato interaction", The Plant Journal, 36:342-352, 2003.
Devaiah SP et al., "Quantitative profiling of polar glycerolipid species from organs of wild-type *Arabidopsis* and a Phospholipase Dα1 knockout mutant", Phytochemistry 67:1907-1924 (Abstract), 2006.

(Continued)

*Primary Examiner* — Maryam Monshipouri
(74) *Attorney, Agent, or Firm* — The PL Law Group, PLLC

(57) ABSTRACT

A method for producing lysophosphatidylethanolamine 18:1 includes extracting phospholipids including mainly phosphatidylethanolamine from a microorganism of *Pseudomonas* sp. and treating the extracted phospholipids with phospholipase A2. An alternative method for producing lysophosphatidylethanolamine 18:1 includes treating a microorganism of *Pseudomonas* sp. directly with phospholipase A2. The lysophosphatidylethanolamine 18:1 can be used as a plant vaccine material for preventing the plants from injuries caused by pathogen infections and/or environmental stresses and accelerating the recovery of plants injured by pathogen infections and/or environmental stresses, and can also be used as a composition for enhancing fruit ripening (color and sweetness) and storage properties, and as it can be used for an application in plant tissues, food products, pharmaceuticals, cosmetics, and agricultural use, it would be very advantageously used in related industries. This invention also provides a method of producing a phosphatidylethanolamine itself from a microorganism of *Pseudomonas* sp.

6 Claims, 29 Drawing Sheets

(56) References Cited

OTHER PUBLICATIONS

Jose J. Reina-Pinto, "Misexpression of Fatty Acid ELONGATION1 in the *Arabidopsis epidermis* Induces Cell Death and Suggests a Critical Role for Phospholipase A2 in This Process", The Plant Cell, vol. 21: 1252-1272, 2009.
Fernando Martinez-Morales et al., "Pathways for phosphatidylcholine biosynthesis in bacteria", Microbiology, 149, 3461-3471, 2003.
Katagiri, Fumiaki et al., "The *Arabidopsis thaliana-Pseudomonas syringae* Interaction", Arabidopsis Book,1:e0039, 2002.

pPLA$_{2\alpha}$::GUS (1.5 h)

Mock    Pst-avrRpm1    Pst

| | WT leaves (12 h) | |
|---|---|---|
| | Mock | LPE |
| PR1 | 1.0 | 15.0 ± 3.0 |
| PDF1.2 | 1.0 | 4.5 ± 1.7 |
| VSP1 | 1.0 | 0.8 ± 0.3 |
| JMT | 1.0 | 1.0 ± 0.4 |

Pst-infected WT leaves (6 d)

Mock      LPE
(sprayed to leaves 12 h before infection)

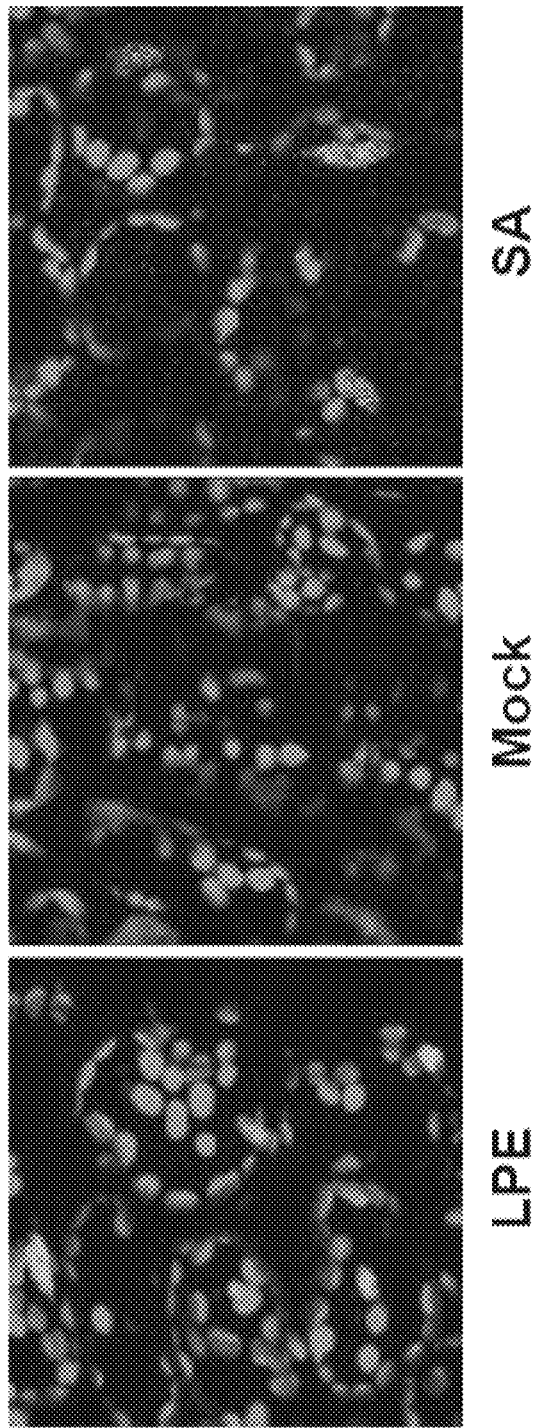

SEQUENCE LISTING

<160> NUMBER OF SEQ ID NOS: 46

<210> SEQ ID NO 1
<211> LENGTH: 23
<212> TYPE: DNA
<213> ORGANISM: Artificial Sequence
<220> FEATURE:
<223> OTHER INFORMATION: primer -continued

<400> SEQUENCE: 1
ggcgatgaag ctcaatccaa acg                                              23

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggtcacgacc agcaagatca agac                                             24

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggggataagg ggttctcaca                                                  20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctgccctagt tacaacccga                                                  20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ggccaaagag ggtatcatcg                                                  20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gctcgaccac agctcttatg g                                                21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
aaagaacatg gtgatcaacg c                                                21

<210> SEQ ID NO 8

```
<211> LENGTH: 20
<212> TYPE: DNA
<213> ORGANISM: Artificial Sequence
<220> FEATURE:
<223> OTHER INFORMATION: primer

<400> SEQUENCE: 8
agttgagatc gcagccactt                                              20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cacccttatc ttcgctgctc                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gttgcatgat ccatgtttgg                                              20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cttaacgtcg gtgttcagct c                                            21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gggtttcttg aggactttgc c                                            21

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
tcgcacttca ttgatgcg                                                18

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
```
tcatagctct gttttcatat cattacct                                          28

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gtcacgtgtt gctttcgg                                                     18

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
aacgtttgaa ctgcttgtg                                                    19

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gctttaggct taaccgtctt                                                   20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
agaaggagaa gggttcatc                                                    19

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gtgctcttgt tcttccctcg                                                   20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
aaggcccacc agagtgtatg                                                   20

<210> SEQ ID NO 21
<211> LENGTH: 23
<212> TYPE: DNA

```
<213> ORGANISM: Artificial Sequence
<220> FEATURE:
<223> OTHER INFORMATION: primer

<400> SEQUENCE: 21
ctcatactca agccaaacgg atc                                         23

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
gccatgaaga tagatgctta att                                         23

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
acctcttctc cgagcatgaa                                             20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gccgtcaaaa acaaccctaa                                             20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
ccataagacg atggagacag c                                           21

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
accgcctcgt gtcactaaag                                             20

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
cgtactaccg gtattgtgct cgact                                       25
```

```
<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
gacaatttca cgctctgctg tgg                                            23

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
gcggttgtgg agaacatgat acg                                            23

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
gaaccaaaca caattcgttg ctg                                            23

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
ctaaccagtc cgaaagacga cctc                                           24

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
cttccttcgt aagtctccct gcc                                            23

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
ggccaaagag ggtatcatcg ag                                             22

<210> SEQ ID NO 34
<211> LENGTH: 23
<212> TYPE: DNA
<213> ORGANISM: Artificial Sequence
<220> FEATURE:
```

```
<223> OTHER INFORMATION: primer

<400> SEQUENCE: 34
cctcactgat actcccacct tcc                                              23

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
caccatggaa atcaacgctc g                                                21

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
ctcagccaac cccctttga tg                                                22

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
gaacttatta gattccttaa cgccgg                                           26

<210> SEQ ID NO 38
<211> LENGTH: 26
<212> TYPE: DNA
<213> ORGANISM: Artificial Sequence
<220> FEATURE:
<223> OTHER INFORMATION: primer

<400> SEQUENCE: 38
ggaaactggt aattgcttcg agaatc                                           26

<210> SEQ ID NO 39
<211> LENGTH: 17
<212> TYPE: DNA
<213> ORGANISM: Artificial Sequence
<220> FEATURE:
<223> OTHER INFORMATION: primer

<400> SEQUENCE: 39
gctttcgacg caccggc                                                     17

<210> SEQ ID NO 40
<211> LENGTH: 26
<212> TYPE: DNA
<213> ORGANISM: Artificial Sequence
<220> FEATURE:
<223> OTHER INFORMATION: primer

<400> SEQUENCE: 40
cgtaacagat acacttgtgt gctggg                                           26
```

```
<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
tccatttcct tgactaaaga atg                                              23

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
agataatcat tattcttgga ttgg                                             24

<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43
catgtgggtt agcgagaagg cta                                              23

<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
ctcactttgg cacatccgag tct                                              23

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
cctcgaatcg aacaccatct                                                  20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ggcaccgtgt cgaagtttat                                                  20
```

METHOD FOR PRODUCING LYSOPHOSPHATIDYLETHANOLAMINE 18:1 FROM MICROORGANISM OF PSEUDOMONAS SP

CROSS REFERENCE TO RELATED APPLICATIONS

The present application is a continuation in part application to International Application No. PCT/KR2015/013227, with an International Filing Date of Dec. 4, 2015, which claims the benefit of Korean Patent Application No. 10-2015-0089016, filed in the Korean Intellectual Property Office on Jun. 23, 2015, the entire contents of which are incorporated herein by reference.

TECHNICAL FIELD

The present invention relates to a method for producing lysophosphatidylethanolamine 18:1 (hereinbelow, also described as LPE18:1) from a microorganism of *Pseudomonas* sp. More specifically, the present invention relates to a method of producing LPE18:1 by treating phospholipids extracted from bacteria microorganism belonging to *Pseudomonas* sp. with phospholipase $A_2$ (hereinbelow also described as $PLA_2$).

BACKGROUND

Lysophosphatidylethanolamine (LPE) is generated by $PLA_2$ enzyme, which hydrolyzes the $2^{nd}$ acyl chain of phosphatidylethanolamine (PE) that is one of the phospholipids forming a cell membrane, and it is present in a small amount in a living body. It has been found that a treatment of LPE can suppress aging of a plant and promote ripening of a fruit (U.S. Pat. No. 5,110,341 and U.S. Pat. No. 5,126,155) and can enhance plant health, protect plants from biotic and abiotic stress-related injuries and enhance the recovery of plant injured as a result of such stresses (U.S. Pat. No. 6,559,099). LPE is mainly produced by treating phosphatidylethanolamine extracted from egg yolk or soy bean with $PLA_2$ enzyme, and the compositional component of LPE is mostly LPE 16:0 and LPE 18:0 in which the $1^{st}$ acyl chain is 16:0 or 18:0. During the process of studying the biological mechanism related to the suppression of aging caused by LPE, it was found that LPE18:1 is a superior molecule which has much higher biological efficacy than LPE 16:0 or LPE 18:0 (U.S. Pat. No. 6,426,105). At present moment, the technique related to the method for producing LPE uses egg yolk or soy bean as a source material so that the component is mostly LPE 16:0 and LPE 18:0 with almost total absence of LPE18:1 (Korean Patent Registration No. 0331932). Accordingly, efforts have been made to find a source material for producing LPE18:1 but to no avail.

In this regard, it is found according to the present invention that the source material (PE containing the $1^{st}$ acyl chain of 18:1) for producing LPE18:1 is present in a microorganism like *Pseudomonas*. The discovery of the source material for producing LPE18:1, and the methods and results of the study are described hereinbelow. Once a plant is infiltrated by a pathogen, a disease-resistant response against part of the pathogen is exhibited by the plant. However, the mechanism related to such response is not clearly known yet. In particular, there is not much information available for the signal transduction mechanism for inducing initial disease resistance. It has been known that, when *Pseudomonas syringae* pv. tomato DC3000 carrying avrRpm1 (hereinbelow, described as Pst-avrRpm1) invades an extracellular space of *Arabidopsis thaliana* (Col-0 ecotype) as a host plant, Avr protein (avrRpm1) is introduced by the pathogen to the cytoplasm of a host through the Type III secretion mechanism. It is known that, if the host cell has RPM1, which is a Resistance protein capable of recognizing avrRpm1 protein, the interaction between those proteins causes an increase in salicylic acid, activation of NPR1 (NON-EXPRESSER OF PR GENES 1), and an immune response for inducing resistance genes like expression of PR (PATHOGENESIS RELATED). However, the upper-level molecule for connecting such gene—for gene interaction, genetic basis, and host immune response for inducing plant resistance genes remain mostly unknown.

According to a study regarding the initial signal transduction that is yet to be known, inventors of the present invention found that LPE18:1 is a signaling molecule to induce disease resistance of a plant. It is surprisingly found that LPE18:1 is mainly produced from an invading pathogen (i.e., *Pseudomonas*). Briefly, the study result indicates that, as *Arabidopsis thaliana* is attacked by non-pathogenic *Pseudomonas* (Pst-avrRpm1), intracellular injection of avrRpm1 protein into plant host cells is yielded, and at that time, the protein factor is recognized as a gene-for-gene interaction by the plant and phospholipase $A_2$-alpha ($PLA_2\alpha$) protein is immediately expressed. $PLA_2\alpha$ protein is secreted to an extracellular region, in which invading pathogens are present, and it decomposes phosphatidylethanolamine present in pathogen membrane to produce LPE18:1 as a main component. This LPE18:1 exhibits an activity of a signaling molecule and, according to propagation to the surrounding, it enters neighboring cells not infected by the pathogen to induce disease resistance.

As it is shown by the study result described above, it was possible to recognize that the source material (PE containing the $1^{st}$ acyl chain of 18:1) for producing LPE18:1 is present in a microorganism like *Pseudomonas*. Thus, the inventors of the present invention carried out large-scale culture of *Pseudomonas* bacteria, and according to extraction of lipids therefrom and treatment with $PLA_2$ enzyme, confirmed production of a large amount of LPE18:1. The LPE18:1 produced by the inventors was applied to a plant, and the biological effect is compared with a known mixture liquid of LPE 16:0/LPE 18:0 and also with commercially available LPE18:1 of high purity. LPE produced by the inventors using the microorganism *Pseudomonas* is found to be mostly consisting of LPE18:1 and LPE 16:0 with extremely small amount of LPE 16:1. In terms of the effect, crude LPE18:1 mixture with LPE16:0 produced by the inventors is superior to LPE 16:0/LPE 18:0 mixture. However, it was inferior to pure LPE18:1. Investigation is also made to see whether or not a source material for producing LPE18:1 can be obtained from a microorganism other than *Pseudomonas*. In this regard, as a result of analyzing phospholipids after separating them from *Escherichia coli* as Gram negative bacteria, *Bacillus subtilis* and *Arthrobacter citres* as Gram positive bacteria, *Saccharomyces cerevisiae* as yeast, and *Chlorella vulgaris* as algae, it is found that, according to the treatment with $PLA_2$, LPE18:1 is produced hardly from other microorganisms but only from *Pseudomonas*.

Meanwhile, "methods of enhancing plant health, protecting plants from biotic and abiotic stress related injuries and enhancing the recovery of plants injured as a result of such stresses" is described in Korean Patent Application Publication No. 2002-0086604, and "a composition and a method for immunizing plants against diseases" is disclosed in Korean Patent Application Publication No. 1997-0001484.

However, the method for producing LPE18:1 from a microorganism of Pseudomonas sp. as described in the present invention has not been disclosed before.

SUMMARY

The present invention is devised under the circumstances described above. Specifically, the inventors of the present invention confirmed that lysophosphatidylethanolamine 18:1 for inducing plant immunity is produced by phospholipase $A_2\alpha$ ($PLA_2\alpha$) from cell membrane phospholipids of Pseudomonas syringae as a pathogen which invades a plant. On the basis of this result, large-scale culture of Pseudomonas (Pst) is carried out followed by extraction of lipids and treatment with $PLA_2$ enzyme, and production of a large amount of LPE18:1 is confirmed. Furthermore, in order to see whether or not a source material (PE containing the $1^{st}$ acyl chain of 18:1) for producing LPE18:1 can be obtained from a microorganism other than Pseudomonas, phospholipids are isolated from Escherichia coli as Gram negative bacteria, Bacillus subtilis and Arthrobacter citres as Gram positive bacteria, Saccharomyces cerevisiae as yeast, and Chlorella vulgaris as algae, and then treated with $PLA_2$. As a result, it is confirmed that not much amount of LPE including LPE18:1 is produced from other microorganisms except Pseudomonas in which significant production of LPE18:1 is shown. Furthermore, in order to see whether or not LPE18:1 can be produced in a large amount from other types belonging to Pseudomonas sp., phospholipids are extracted from Pseudomonas caeni, Pseudomonas fluorescens, and Pseudomonas putida. As a result, it is found that content of PE containing the $1^{st}$ acyl chain of 18:1 as an original source material of LPE18:1 is quite high in all types of Pseudomonas, and LPE18:1 is produced in a large amount according to a treatment with $PLA_2$ enzyme.

According to the present invention, the Pseudomonas microorganism is cultured at large scale, and phospholipids are extracted and treated with $PLA_2$ obtained from an animal. As a result, it is confirmed that LPE18:1 can be produced in a large amount, and the present invention is completed accordingly.

In order to solve the problems described above, the present invention provides a method for producing LPE18:1 according to treatment of phospholipids extracted from a microorganism of Pseudomonas sp. with phospholipase $A_2$.

According to the present invention, it is confirmed that the crude LPE18:1 mixture is produced by phospholipase $A_2\alpha$ from cell membrane phospholipids of a pathogen which invades a plant, and a local immune response of a plant is induced as a result. As a result, the crude LPE18:1 mixture produced by the treatment with phospholipase $A_2\alpha$ of the present invention is a material originating from natural products. LPE18:1 can be used as a plant vaccine material for preventing the plants from injuries caused by pathogen infections and/or environmental stresses and accelerating the recovery of plants injured by pathogen infections and/or environmental stresses. LPE18:1 can also be used as a composition for enhancing fruit ripening (color and sweetness) and storage properties, and as it can be used for an application in plant tissues, food products, pharmaceuticals, cosmetics, and agricultural use, it would be very advantageously used in related industries.

BRIEF DESCRIPTION OF THE DRAWINGS

FIGS. 1A and 1B are the photographic images in which, unlike the wild type plant, symptoms of the disease are exhibited beyond the hypersensitive response area in the whole plant (A) and leaf (B) of pla2α (knock out) and pla2α-II (knock down) mutant plant 6 days after Pst-avrRpm1 infiltration. FIG. 1C is a graph illustrating the ion leakage 15 hours after the infiltration of Pst-avrRpm1 (avrRpm1), Pst-avrRpt2 (avrRpt2), Pst-avrRps4 (avrRps4) and virulent Pst (Pst) in the leaf of the wild type plant and pla2α mutant plant—NT: control group with no treatment. FIG. 1D is a graph illustrating the gene expression levels of PR1 and PDF1.2 in the plant 24 hours after Pst-avrRpm1 infiltration (*P<0.05). FIG. 1E is a graph illustrating the result of bacterial growth assay with Pst-avrRpm1 and Pst in pla2α mutant plant and also in pla2α mutant plant ($PLA_2\alpha$/pla2α) which has been complemented with native-promoter::$PLA_2\alpha$ (*P<0.05, P<0.01). FIG. 1F is a graph illustrating the result of bacterial growth assay with Pst-avrRpt2 and Pst-avrRps4 in the wild plant and pla2α mutant plant (P<0.01).

FIG. 2A shows the result illustrating the expression of $PLA_2\alpha$ in the wild type plant inoculated with Pst-avrRpm1 (avrRpm1), FIG. 2B is a photographic image showing the analyzed GUS activity in Arabidopsis plant which has been transformed with $PLA_2\alpha$ promoter::GUS, 1.5 hours after the infiltration with Pst-avrRpm1 and Pst, FIG. 2C is a graph showing the result of analyzing the lipid metabolites which have been produced in the wild type plant, 3 hours after pathogen inoculation, FIG. 2D is a graph showing the result of analyzing the lipid metabolites in pla2α mutant plant after pathogen inoculation, or pathogen inoculation followed by infiltration with recombinant $PLA_2\alpha$ protein, FIG. 2E is a graph showing the result of levels of each LPE species in the wild type leaf 3 hours after treatment with mock or Pst-avrRpm1. FIG. 2F is a graph showing the result of analyzing the LPE species that are released by recombinant $PLA_2\alpha$ protein from a mixture suspension when $rPLA_2\alpha$ protein was mixed with live Pst-avrRpm1, bacterial lipid extract or leaf tissues, and FIG. 2G is a graph showing the antibacterial activity of recombinant $PLA_2\alpha$ protein in which, to the culture media of Pst, M represents a mock treatment, P represents a treatment with $PLA_2\alpha$ protein, PM represents a treatment with a mixture of $PLA_2\alpha$ protein and manoalide, and PMM represents a treatment with a mixture of $PLA_2\alpha$ protein and manoalide buffer (ethanol) (*P<0.05, **P<0.01). Furthermore, FIG. 2H is a graph showing the result of determining the radiolabeled LPE levels released from invading bacteria, 3 hours after inoculation of radiolabeled Pst-avrRpm1 to a leaf of the wild type plant.

FIGS. 3A to 3F show the result illustrating the recovery of the local immune response in pla2α mutant plant by supplementation of exogenous LPE18:1, in which FIG. 3A is a photographic image for showing the recovery of phenotypic defect of pla2α mutant plant by treatment of LPE18:1 but not by treatment of LPC (lysophosphatidylcholine) or LPG (lysophosphatidylglycerol), FIG. 3B is a graph of bacterial growth assay illustrating that the impaired local immunity of pla2α mutant plants is complemented by LPE but only a little by LPG., FIG. 3C shows a result of analyzing the gene expression levels of PR1 gene and other wound-related genes in the wild type leaf which has been treated with mock treatment or LPE, FIG. 3D shows the result illustrating the acquirement of local immunity in the wild type plant and pla2α mutant plant by a treatment with only LPE, FIG. 3E is a photographic image illustrating the enhanced disease resistance against virulent Pst, which explains the acquirement of local immunity caused by LPE, and FIG. 3F is a graph showing the result of an in vitro analysis which has been carried out to see whether or not LPE itself has an antibacterial activity against Pst (*P<0.05, **P<0.01).

FIGS. 4A to 4E show the result of confirming ICS1-dependent biosynthesis of salicylic acid and NPR1 activation caused by LPE, in which FIGS. 4A and 4C show the result illustrating the gene expression levels, and FIGS. 4B and 4D show the result of analyzing salicylic acid levels. FIG. 4E is an image showing location change of NPR1 from cytoplasm to nucleus after treatment of a transgenic plant carrying 35S::NPR1-eGFP with mock, LPE, or salicylic acid.

FIGS. 5A to 5F shows the result of confirming ethylene-dependent expression of PDF1.2 that is mediated by $PLA_2\alpha$ protein and LPE, in which FIGS. 5A and 5D show a change in gene expression levels, FIGS. 5B and 5E show the synthesis levels of ethylene, and FIGS. 5C and 5F show the result of analyzing the synthesis levels of jasmonic acid (*P<0.05, **P<0.01).

FIGS. 6A and 6B show the result illustrating the bacterial growth after inoculation of Pst-avrRpm1 in which the result is shown for different growth conditions (SD, short-day condition with 9 hours of light period: LD, long-day condition with 16 hours of light period) and maturity levels of leaves (*P<0.05, **P<0.01). FIG. 6C shows the result for confirming the gene expression of ICS1 and PR1 after infiltration of a buffer, Dsbc, or $PLA_2\alpha$ protein into pla2α mutant plant. FIG. 6D shows the result of analyzing the PR1 gene expression in a group with mock treatment, or a treatment with $PLA_2\alpha$ protein, or a treatment with $PLA_2\alpha$ protein together with an inhibitor (Mano). FIG. 6E shows the result of analyzing bacterial growth in the wild type plant and pla2α mutant plant after pretreatment with $PLA_2\alpha$ inhibitor followed by inoculation of Pst-avrRpm1. FIG. 6F shows the result of analyzing bacterial growth in which the analysis is made after transforming pla2α mutant plant with a vector having a structure of $PLA_2\alpha$ (no S.P. $PLA_2\alpha/PLA_2\alpha$), which remains in the cytoplasm as it cannot secrete apoplast due to lack of a signal peptide, followed by inoculation of Pst-avrRpm1.

DETAILED DESCRIPTION

Figure 1A:
FIGS. 1A to 1F show the result illustrating damaged local immunity in pla2α mutant plant.

In order to achieve the purpose of the present invention, the present invention provides a method for large scale production of lysophosphatidylethanolamine comprising:
(a) performing large scale culture of a microorganism of Pseudomonas sp. followed by harvesting the microorganism and extracting phospholipids from the microorganism;
(b) treating the phospholipids extracted in the step (a) with phospholipase $A_2$ to produce lysophosphatidylethanolamine, and
(c) separating and purifying the lysophosphatidylethanolamine produced in the step (b).

For the method according to one embodiment of the present invention, the lysophosphatidylethanolamine (hereinbelow, described as LPE) is produced by phospholipase $A_2$ protein from phospholipids of a cell membrane of pathogen which invades a plant, and LPE can be LPE 16:0, LPE 16:1, LPE 18:0, LPE18:1, LPE 18:2, or LPE 18:3. LPE can be preferably LPE 16:0, LPE 16:1, or LPE18:1, and more preferably LPE18:1, but not limited thereto.

Furthermore, for the method of the present invention, the microorganism may be a microorganism of Pseudomonas sp. It is preferably Pseudomonas caeni, Pseudomonas fluorescens, Pseudomonas putida, or Pseudomonas syringae. It is more preferably Pseudomonas caeni or Pseudomonas fluorescens, but not limited thereto.

Furthermore, for the method of the present invention, the phospholipids may be phosphatidylcholine, phosphatidylserine, or phosphatidylethanolamine, preferably phosphatidylethanolamine, and more preferably phosphatidylethanolamine in which the acyl chain at the first position is 18:1, but not limited thereto.

For the method according to one embodiment of the present invention, the phospholipase $A_2$ is an enzyme which hydrolyzes the ester bond at sn-2 position of glycerol phospholipid as a main component of a biological membrane to release lysophospholipids and fatty acids. Phospholipase $A_2$ may be an enzyme originating from an animal such as snake toxin, honey bee toxin, or pig pancreatic juice, or from a microorganism or a plant. It can be also a recombinant protein, but not limited thereto.

Furthermore, for the method of the present invention, any method well known in the pertinent art can be used as a method for extracting phospholipids from harvested bacteria and a method for separating and purifying lysophosphatidylethanolamine.

The present invention further provides lysophosphatidylethanolamine produced by the aforementioned method. Lysophosphatidylethanolamine produced by the method of the present invention is preferably lysophosphatidylethanolamine 18:1, but not limited thereto.

Hereinbelow, the present invention is explained in greater detail in view of the Examples. However, it is evident that the following Examples are given only for exemplification of the present invention and by no means the present invention is limited to the following Examples.

Materials and Methods

Plant Materials and Chemical Reagents

*Arabidopsis* plant was cultivated at temperature of 22° C. and relative humidity of 60% with conditions including 16 hours of light period and 120 µmoles $m^{-2}s^{-1}$ of photon flux density. Because the plant defense response is age-dependent, fully mature leaves of the 4 week old plant were used for various analyses. *Arabidopsis* (*Arabidopsis thaliana*) mutants including pla2α, pla2α-II, sid2, npr1-5, rps2 and ein2 (Salk_099415, CS857021, Salk_042603, CS3724, Salk_087581, CS3071 and CS8072, respectively) were purchased from *Arabidopsis* Biological Resource Center, USA. *Arabidopsis* mutants eds1 and pad4-5 were obtained from S. A. Whitham (Iowa State University, USA) and J. E. Parker (Max Planck Institute for Plant Breeding Research, Germany), respectively. The transgenic line expressing NPR1-eGFP and NahG were obtained from X. Dong (Duke University, USA) and O. M. Park (Korea University, South Korea), respectively.

Complementarity Test of pla2α Mutant Carrying Native-Promoter::$PLA_2α$ and Generation of $PLA_2α$ Overexpressing Transgenic Event For complementation, pla2α mutant plant was transfected by a floral dip method by using pCAMBIA1300 clone, which is a binary vector for plant transfection including $PLA_2α$ genomic DNA having native promoter part (i.e., from −1175 to +922) at BamHI site. In order to have an artificial deformation for intracellular translocation of $PLA_2α$ (i.e., not allowing secretion to apoplast), pCAMBIA1300 carrying $pPLA_2α$::$PLA_2α$ with no signal peptide was prepared, and introduced to pla2α plant by using *Agrobacterium*. To generate $PLA_2α$-overexpressing transgenic event, pBIG binary vector carrying p35S::$PLA_2α$ was introduced to the wild type plant.

Bacterial Inoculation to Plant

*Pseudomonas syringae* pv. tomato DC3000 (hereinbelow, Pst) and Pst-avrRpm1, which is avrRpm1-containing bacterial strain with no virulency, were obtained from Y. J. Kim (Korea University, South Korea). Pst-avrRpt2, which is avrRpt2-containing bacterial strain with no virulency, was obtained from J. M. Park (KRIBB, South Korea) and Pst-avrRps4, which is avrRps4-containing bacterial strain with no virulency, was obtained from R. Innes (Indiana University, USA). The bacterial strains were cultured and treated according to the method of Katagiri, et al. (*Arabidopsis Book*, 2002, 1:e0039).

Gene Expression Analysis

Total RNA was extracted by using RNA isolator (Gibco, USA) from a sample which has been frozen with liquid nitrogen (i.e., 2 leaves per sample). Reverse transcription polymerase chain reaction (RT-PCR) and real-time quantitative polymerase chain reaction (real-time qPCR) were carried out by using gene-specific primers. For the analysis of a real-time quantitative polymerase chain reaction, Applied Biosystems 7900 Real-Time PCR SYSTEM™ was used. 2×SYBR® Green qPCR master mix was used for PCT amplification. The analyzed data were normalized first against the amount of ACTIN1 gene, and the fold increase of gene expression according to treatment was determined in comparison with a mock or non-treatment plant (1.0 fold). Reference gene as an alternative (AT1G13320) was obtained from the previous study (Hong et al., 2010, *Plant Cell Physiol.* 51:1694-1706). The gene-specific primers that are used in the present invention are as described in Table 1 and Table 2 below.

TABLE 1

Primers for RT-PCR

| Gene name | Forward direction (5'→3') (SEQ ID NO:) | Reverse direction (5'→3') (SEQ ID NO:) |
| --- | --- | --- |
| ACTIN1 | GGCGATGAAGCTCAATCCAAACG (SEQ ID NO 1) | GGTCACGACCAGCAAGATCAAGAC (SEQ ID NO 2) |
| ICS1 | GGGGATAAGGGGTTCTCACA (SEQ ID NO 3) | CTGCCCTAGTTACAACCCGA (SEQ ID NO 4) |
| JMT | GGCCAAAGAGGGTATCATCG (SEQ ID NO 5) | GCTCGACCACAGCTCTTATGG (SEQ ID NO 6) |
| PAL1 | AAAGAACATGGTGATCAACGC (SEQ ID NO 7) | AGTTGAGATCGCAGCCACTT (SEQ ID NO 8) |
| PDF1.2 | CACCCTTATCTTCGCTGCTC (SEQ ID NO 9) | GTTGCATGATCCATGTTTGG (SEQ ID NO 10) |
| PLA2α | CTTAACGTCGGTGTTCAGCTC (SEQ ID NO 11) | GGGTTTCTTGAGGACTTTGCC (SEQ ID NO 12) |

TABLE 1-continued

Primers for RT-PCR

| Gene name | Forward direction (5'→3') (SEQ ID NO:) | Reverse direction (5'→3') (SEQ ID NO:) |
|---|---|---|
| PLA2β | TCGCACTTCATTGATGCG (SEQ ID NO 13) | TCATAGCTCTGTTTTCATATCATTACCT (SEQ ID NO 14) |
| PLA2γ | GTCACGTGTTGCTTTCGG (SEQ ID NO 15) | AACGTTTGAACTGCTTGTG (SEQ ID NO 16) |
| PLA2δ | GCTTTAGGCTTAACCGTCTT (SEQ ID NO 17) | AGAAGGAGAAGGGTTCATC (SEQ ID NO 18) |
| PR1 | GTGCTCTTGTTCTTCCCTCG (SEQ ID NO 19) | AAGGCCCACCAGAGTGTATG (SEQ ID NO 20) |
| VSP1 | CTCATACTCAAGCCAAACGGATC (SEQ ID NO 21) | GCCATGAAGATAGATGCTTAATT (SEQ ID NO 22) |

TABLE 2

Primers for Real-Time qRT-PCR

| Gene name | Forward direction (5'→3') (SEQ ID NO:) | Reverse direction (5'→3') (SEQ ID NO:) |
|---|---|---|
| ACS2 | ACCTCTTCTCCGAGCATGAA (SEQ ID NO 23) | GCCGTCAAAAACAACCCTAA (SEQ ID NO 24) |
| ACS6 | CCATAAGACGATGGAGACAGC (SEQ ID NO 25) | ACCGCCTCGTGTCACTAAAG (SEQ ID NO 26) |
| ACTIN1 | CGTACTACCGGTATTGTGCTCGACT (SEQ ID NO 27) | GACAATTTCACGCTCTGCTGTGG (SEQ ID NO 28) |
| AT1G13320 | GCGGTTGTGGAGAACATGATACG (SEQ ID NO 29) | GAACCAAACACAATTCGTTGCTG (SEQ ID NO 30) |
| ICS1 | CTAACCAGTCCGAAAGACGACCTC (SEQ ID NO 31) | CTTCCTTCGTAAGTCTCCCTGCC (SEQ ID NO 32) |
| JMT | GGCCAAAGAGGGTATCATCGAG (SEQ ID NO 33) | CCTCACTGATACTCCCACCTTCC (SEQ ID NO 34) |
| LOX2 | CACCATGGAAATCAACGCTCG (SEQ ID NO 35) | CTCAGCCAACCCCCTTTTGATG (SEQ ID NO 36) |
| PAL1 | GAACTTATTAGATTCCTTAACGCCGG (SEQ ID NO 37) | GGAAACTGGTAATTGCTTCGAGAATC (SEQ ID NO 38) |
| PDF1.2 | GCTTTCGACGCACCGGC (SEQ ID NO 39) | CGTAACAGATACACTTGTGTGCTGGG (SEQ ID NO 40) |
| PLA2α | TCCATTTCCTTGACTAAAGAATG (SEQ ID NO 41) | AGATAATCATTATTCTTGGATTGG (SEQ ID NO 42) |
| PR1 | CATGTGGGTTAGCGAGAAGGCTA (SEQ ID NO 43) | CTCACTTTGGCACATCCGAGTCT (SEQ ID NO 44) |
| VSP1 | CCTCGAATCGAACACCATCT (SEQ ID NO 45) | GGCACCGTGTCGAAGTTTAT (SEQ ID NO 46) |

Histochemical Analysis of GUS Activity and Translocation of PLA$_2$α to Apoplast To have histochemical localization of GUS activity, transgenic *Arabidopsis* plant carrying PLA$_2$α-promoter::GUS structure was generated (Jung et al., 2012, *Front Plant Sci.* 3:126). To have clear expression of PLA$_2$α in an infected area of a leaf tissue, 3 hours after switching to night condition by turning off the light, the pathogen was syringe-infiltrated to an abaxial surface of the PLA$_2$α-promoter::GUS transgenic *Arabidopsis* leaf 1.5 Hours later, histochemical analysis of GUS was carried out according to the method by Jefferson (*EMBO J.* 1987, 6:3901-3907).

Lipid Extraction from Leaves and Bacteria, and ESI-MS/MS Analysis

According to the method described before (Ryu et al., 1996, *Biochem Biophys Acta.* 1303:243-250), total lipid was extracted from leaf and bacterial samples. Each phospholipid and free fatty acid (FFA) were quantified by Kansas Lipidomics Research Center based on ESI-MS/MS analysis.

Treatment with Lipid, Salicylic Acid, and Recombinant PLA$_2\alpha$ Protein

Every phospholipid was purchased from Avanti Polar Lipids Inc. (USA), and free fatty acids (16:0, 18:0 and 18:1) were purchased from Sigma Co. (USA). The solvent was dried under nitrogen gas stream, and the lipids were suspended therein according to ultrasonication so as to have final concentration of 100 nmol ml$^{-1}$ in 0.018% silwet L-77 (or 200 nmol ml$^{-1}$ in H$_2$O). Among the LPE (lysophosphatidylethanolamine) species, LPE18:1 showed the biggest increase in Pst-avrRpm1 inoculation, and thus it is used for the present invention.

The mature form of the recombinant PLA$_2\alpha$ protein was produced in *Escherichia coli* which is fused with Dsbc protein. According to the method described before (Ryu et al., 2005, *Biochem Biophys Acta*. 1736:144-151), it was purified by affinity chromatography. The protein mixture in which PLA$_2\alpha$ and Dsbc are separated from each other or Dsbc:PLA$_2\alpha$ fusion protein (10 μgml$^{-1}$) was treated on the leaf of pla2α mutant by syringe infiltration, each in an amount of 0.5 μg. The enzyme activity of PLA$_2\alpha$ was determined by in vitro analysis using substrate PE for a reaction mixture containing 10 mM Ca$^{2+}$ and 0.05% Triton X-100 in 50 mM Tris-HCl (pH 8.5). The mock-treated plant was infiltrated with a buffer (50 mM Tris-HCl, pH 8.0) or Dsbc protein. For inactivation of the PLA$_2\alpha$ activity, recombinant PLA$_2\alpha$ was pre-treated for 30 minutes at 30° C. with 2 μM manoalide as an irreversible inhibitor. Inactivation of the PLA$_2\alpha$ activity caused by manoalide was confirmed by an in vitro analysis of PLA$_2$ activity.

Antibacterial Activity of PLA$_2\alpha$ and Release of Lipid Metabolites from Bacteria In order to determine the antibacterial activity of PLA$_2\alpha$, 3 μg of recombinant PLA$_2\alpha$ in free and mature form, which has been prepared according to the method by Ryu et al. (*Biochem Biophys Acta*. 2005, 1736:144-151), was added to 100 μl of a solution (Tris-HCl (50 mM, pH 8.0), 10 mM calcium chloride (CaCl$_2$)) in which virulent Pst (5×10$^5$ CFU ml$^1$) is suspended. The bacteria sample was cultured in a weak shaking state at 28° C. for 6 hours. Thereafter, only the survived bacteria were titrated. As a mock control group, a suspension in which the bacteria are suspended in a solution having no PLA$_2\alpha$ was used.

Quantification of Salicylic Acid, Ethylene, and Jasmonic Acid, and NPR1 Transition According to the method described before (Bowling et al., 1994, *Plant Cell* 6:1845-1857; Heck et al., 2003, *Plant J.* 36:342-352), salicylic acid, ethylene, and jasmonic acid were quantified from 0.5 g of a *Arabidopsis* leaf sample which has been sprayed with Pst-avrRpm1 suspension (1×10$^8$ CFU ml$^{-1}$ in 0.018% Silwet L-77) or LPE (100 nmol ml$^{-1}$ in 0.018% Silwet L-77 or 200 nmol ml$^{-1}$ in H$_2$O).

NPR1 transition was determined by spraying LPE (100 nmol ml$^{-1}$ in 0.018% Silwet L-77), salicylic acid (0.3 mM in 0.018% Silwet L-77), or mock solution (0.018% Silwet L-77) to a transgenic plant carrying 35S::NPR1-eGFP, and observing, 6 hours later, the plant leaf with a laser scanning confocal microscope (Zeiss, Germany).

Analysis of Ion Leakage

Leaf tissue (i.e., 4 leaves for each sample) was collected, and after vacuum infiltration for 5 minutes with sterilized water, they were cultured at room temperature for 2 hours under shaking. Level of electrolyte leakage from the sample was measured by using a conductivity meter (Mettler Toledo, Switzerland). Data appeared to be the percentage of total electrolyte leakage was obtained by, after freezing, carrying out melting at room temperature under shaking for 6 hours.

Statistics

Student's t-test was employed to determine the statistical significance among groups. The data of bacterial growth analysis and ion leakage analysis were expressed in terms of mean±standard deviation, and the significant value was as follows: *P<0.05; **P<0.01. All data other than those were expressed in terms of mean±standard error in which *P<0.05; **P<0.01.

Production of LPE18:1 by rPLA$_2$ Protein from *Pseudomonas* Lipid Extract

*Pseudomonas* cell culture was freeze-dried, and total lipids were extracted from the bacteria according to the method described before (Ryu et al., 1996, *Biochem Biophys Acta*. 1303:243-250). Thereafter, commercially available phospholipase A$_2$ (powder form) was dissolved in water and 20 μl was collected. A mixture of the *Pseudomonas* lipid extract (20 μl), phospholipase A$_2$ enzyme (20 μl), and the reaction buffer (50 mM Tris-HCl, 10 mM CaCl$_2$, 0.05% Triton X-100) (160 μl) was allowed to react for 30 minutes at 30° C. Thereafter, 750 μl of Chl:MeOH (1:2) was added thereto to terminate the reaction. By adding 200 μl of chloroform and 200 μl of KCl (2 M) thereto followed by centrifugation and removal of supernatant, LPE18:1 was obtained. Production of LPE18:1 by PLA$_2$ protein treatment was achieved not only form the lipid extract of *Pseudomonas* but also directly from live or dead *Pseudomonas* itself. The simplest way was that live *Pseudomonas* was treated with phospholipase A$_2$ enzyme and the product, LPE, released out of the bacteria into the reaction buffer was obtained by collecting the solution.

Figure 1B:
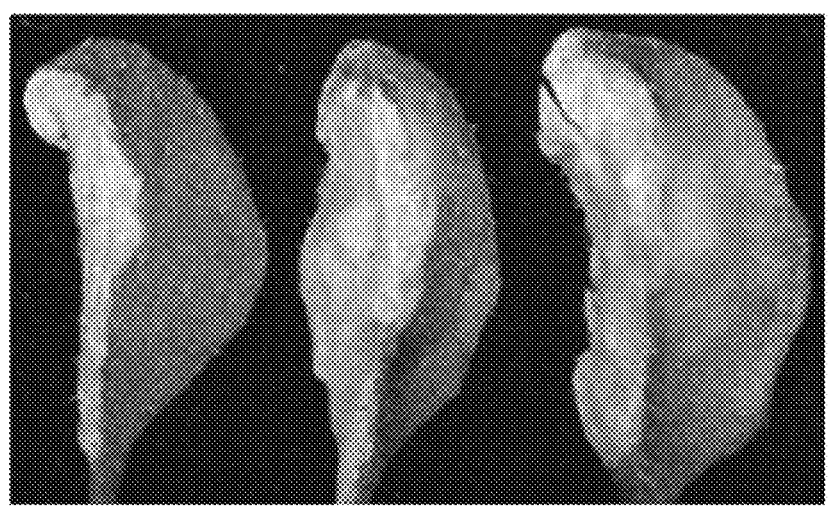
Figure 1C:
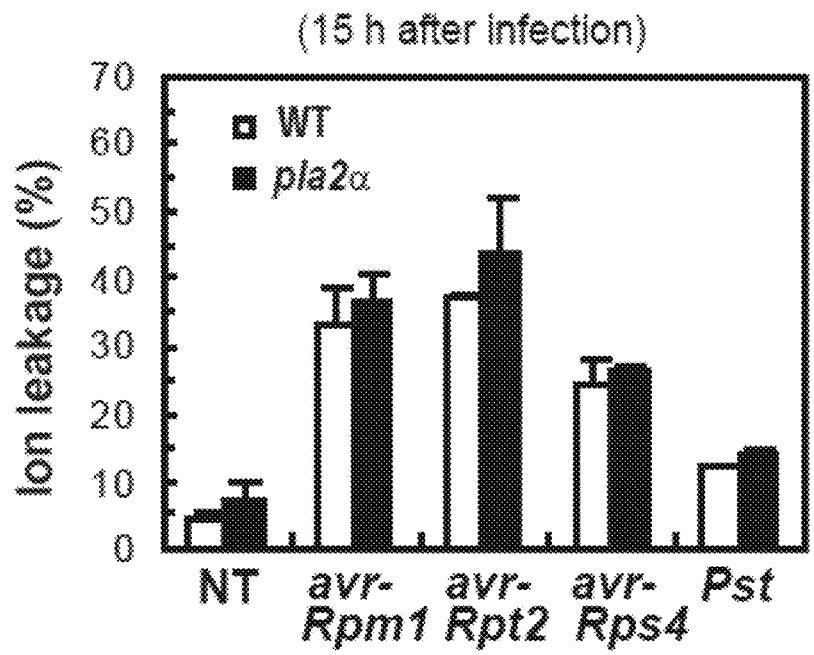
Figure 1D:
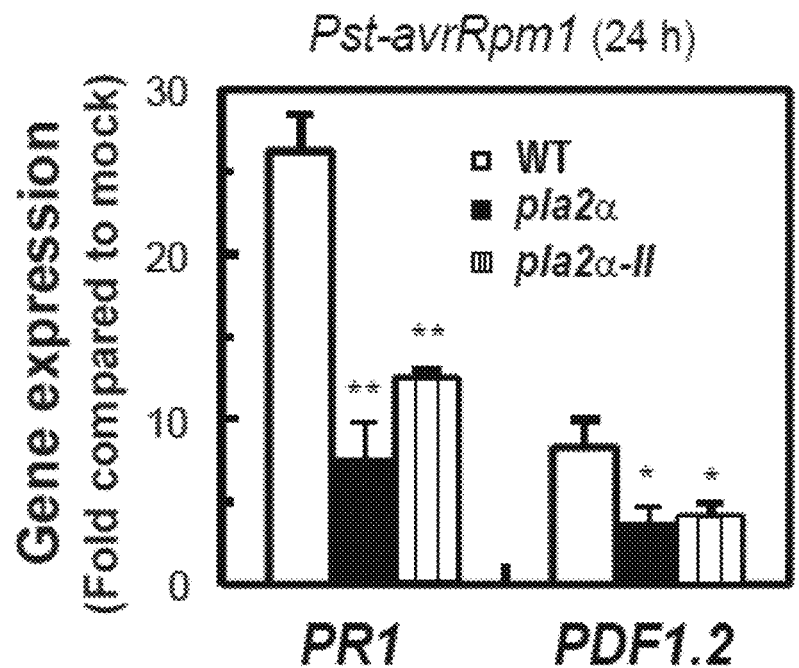
Figure 1E:
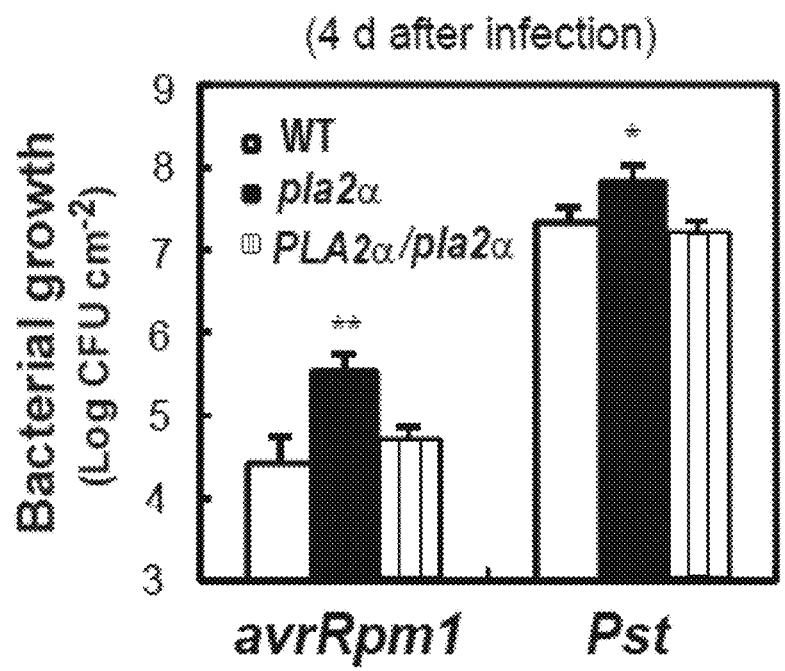
Figure 1F:
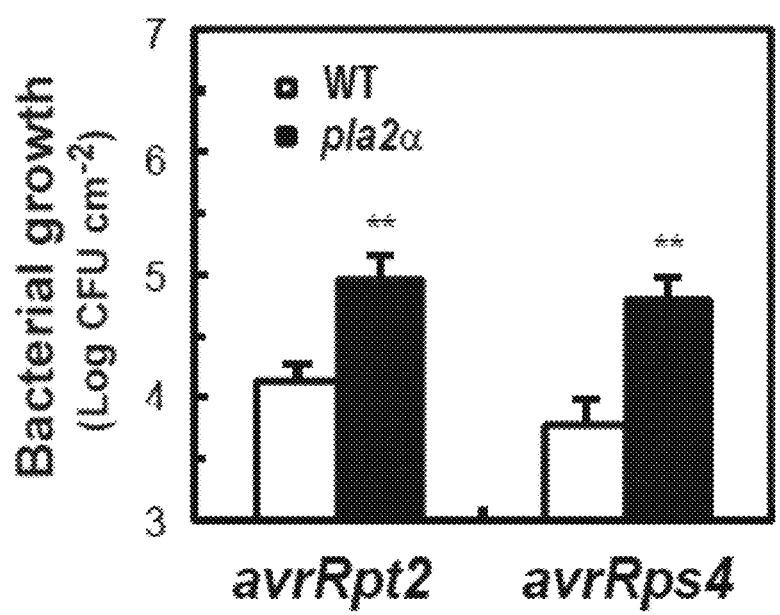

Example 1. Local Resistance Gene-Induced Immune Responses are Impaired in pla$_2\alpha$ Mutants In order to identify the cellular function(s) of secretory PLA$_2\alpha$ in plant defense responses, the pla2α mutants, pla2α (knockout) and pla2α-II (knockdown), were obtained from TAIR. Under normal growth conditions, the pla2α mutants did not differ phenotypically from wild-type plants. However, the local immune responses of the pla2α mutants to Pst-avrRpm1 were impaired (FIGS. 1A, 1B, ID and IE). Basal resistance of the mutant to virulent Pst was also impaired (FIG. 1E). Although pla2α mutants exhibited an apparently normal hypersensitive response (HR) to the avirulent bacteria (FIG. 1C), they failed to adequately restrict bacterial growth compared to wild type plants (FIGS. 1B and 1E). qRT-PCR analysis also showed that the pla2α mutant plants had much lower Pst-avrRpm1-induced expression of defense genes such as PR1 and PDF1.2 than wild type plants (FIG. 1D). When the pla2α mutant was complemented with the native-promoter::PLA$_2\alpha$ construct, however, its ability to restrict Pst-avrRpm1 growth and to express defense genes was restored (FIG. 1E). The pla2α mutant was also unable to mount a local immune response when inoculated with Pst-avrRpt2 or Pst-avrRps4 (FIG. 1F). These results suggest that PLA$_2\alpha$ is involved in the immune responses induced by both CC-NB-LRR and TIR-NB-LRR type R genes.

Figure 2A:
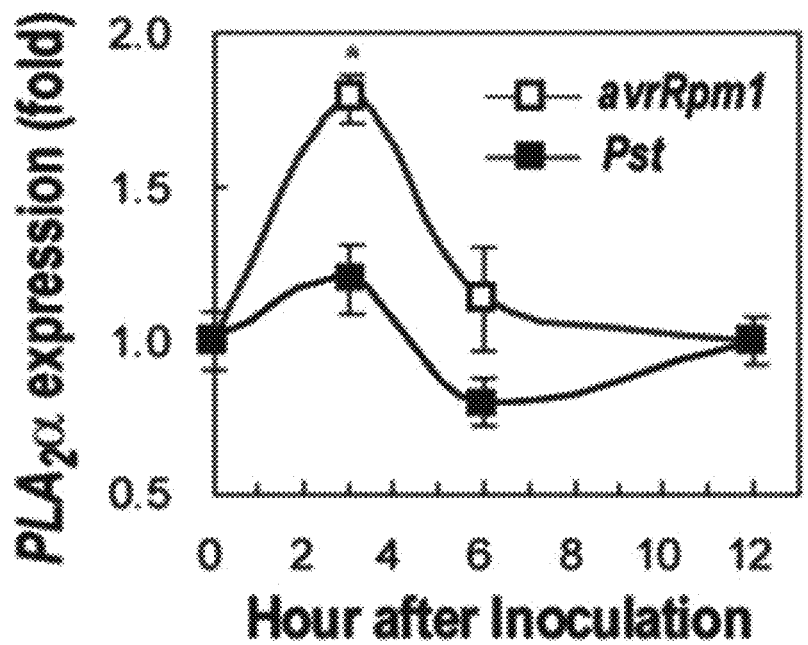
FIGS. 2A to 2H show the result illustrating the expression of native $PLA_2\alpha$ and occurrence lipid metabolites like LPE. Specifically.
Figure 2B:
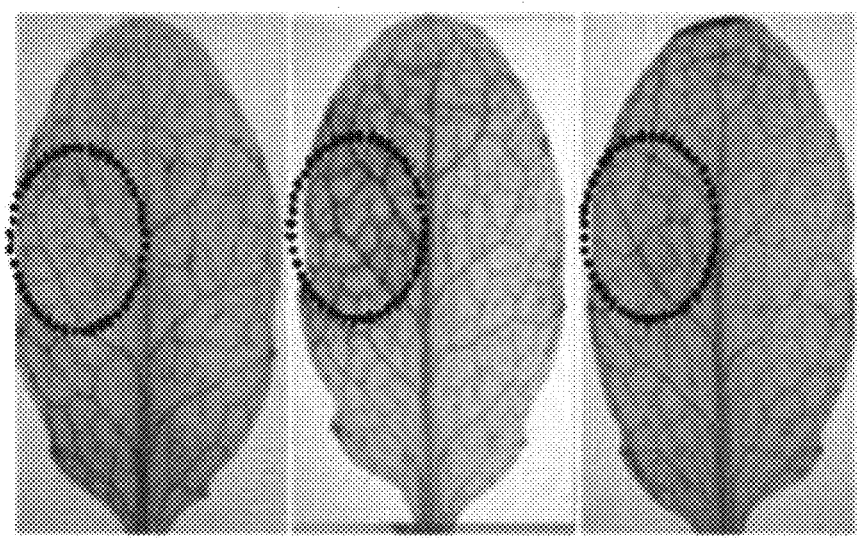
Figure 2C:
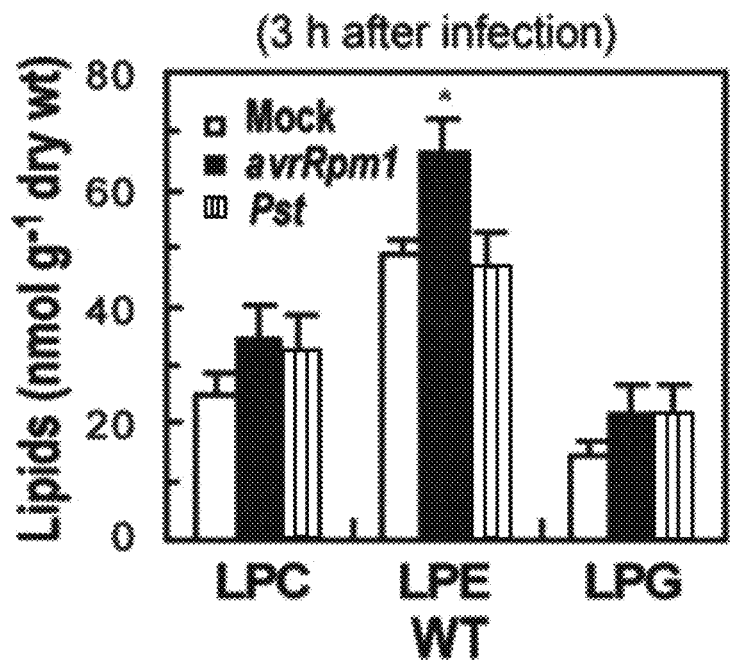
Figure 2D:
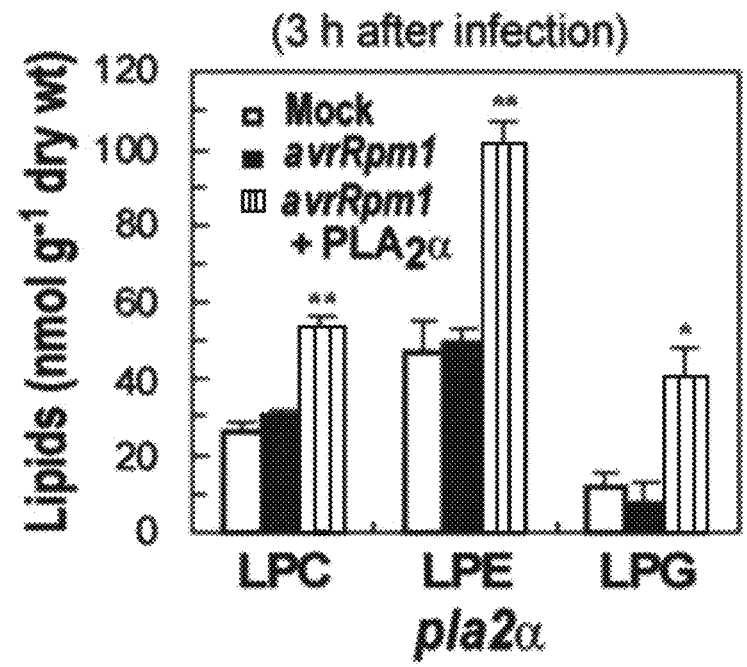
Figure 2E:
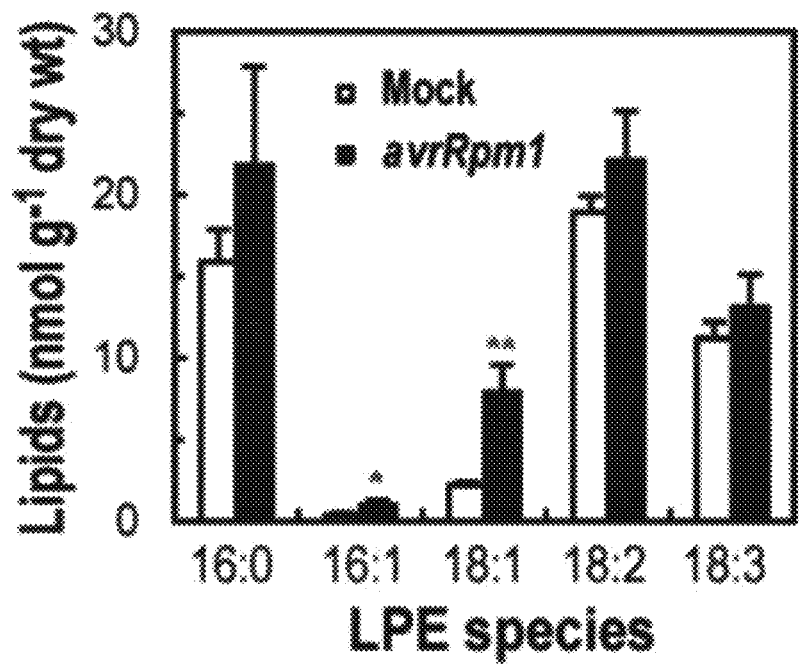
Figure 2F:
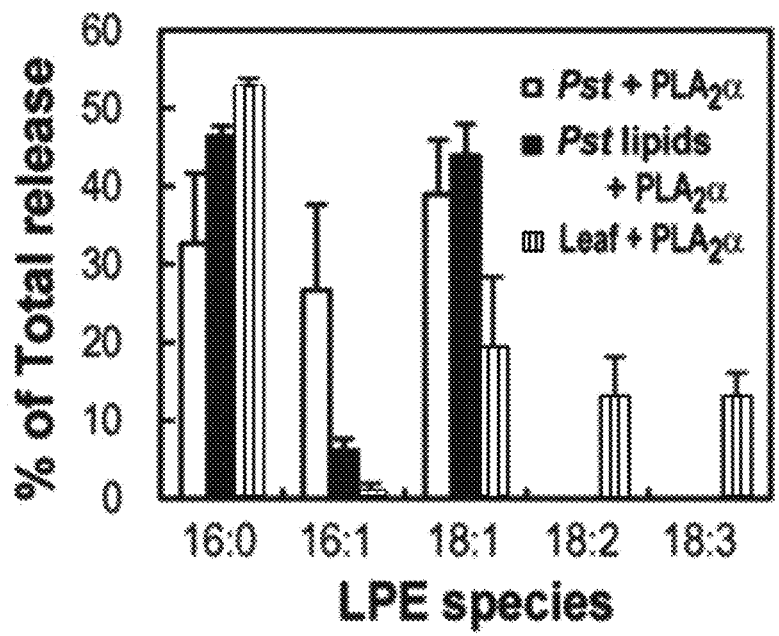
Figure 2G:
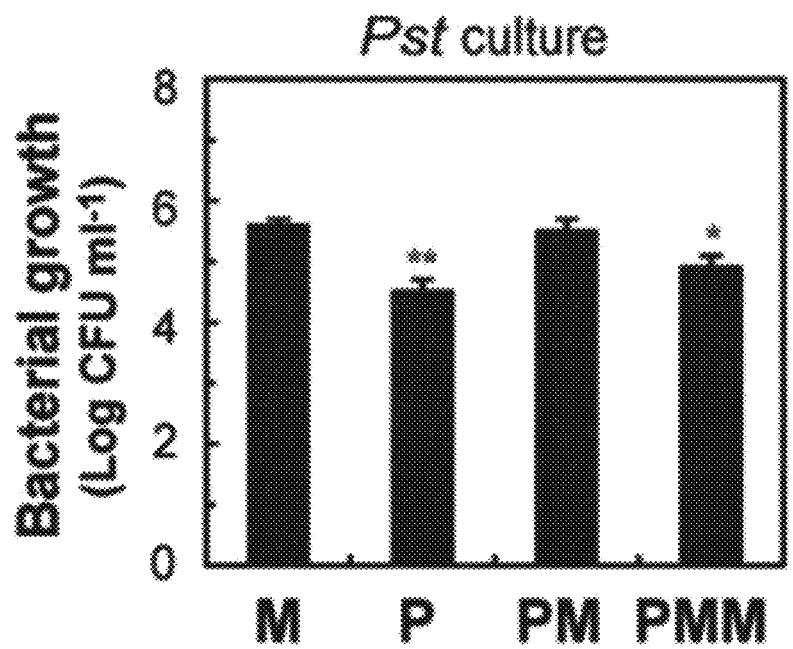
Figure 2H:
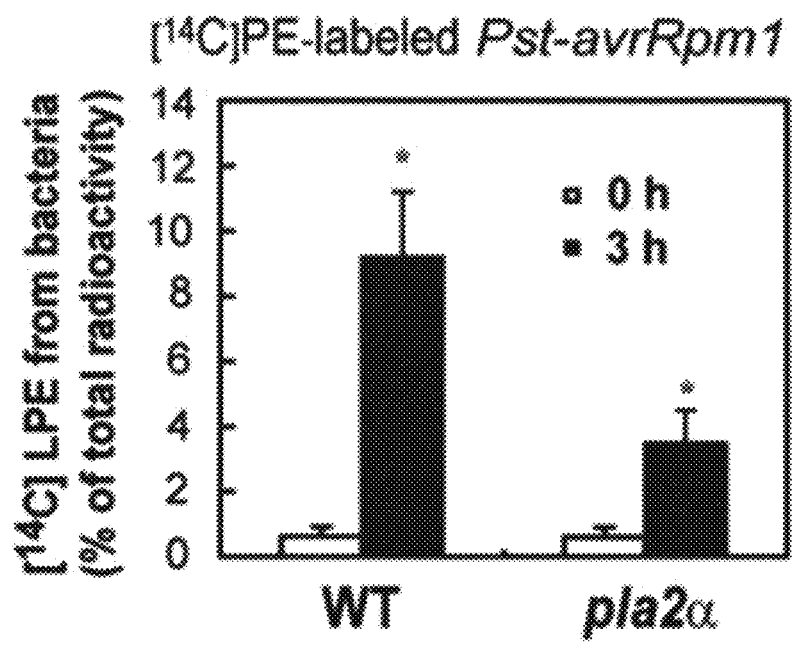

Example 2. Resistance Gene-Mediated Expression of PLA$_2\alpha$ is Followed by an Increase of LPE Levels In Col-0 wild type plants, PLA$_2\alpha$ is expressed at low levels. PLA$_2\alpha$ expression is rapidly and moderately induced upon inoculation with Pst-avrRpm1, but weakly in response to virulent Pst inoculation (FIG. 2A), which suggests that its expression is R gene-mediated. Similar results were also observed with pPLA$_2$α::GUS assay in which PLA$_2$α promoter was activated in response to the inoculation of Pst-avrRpm1 but not to that of virulent Pst (FIG. 2B). PLA$_2$α is then secreted to the apoplast, where it may generate lysophospholipids and free fatty acids from membrane phospholipids. As expected, significant increases in the lipid products of PLA$_2$α, such as LPE, were detected by 3 h post-inoculation of Pst-avrRpm1 in Col-0 wild type plants as compared to mock-inoculated plants (FIG. 2C). Slight increases in lysophosphatidylglycerol (LPG) and lysophosphatidylcholine (LPC) were also detected. When virulent Pst was inoculated, there was no increase in LPE, but slight increases only in LPC and LPG were detected (FIG. 2C). These results indicate that enhanced production of LPE is a specific response to inoculation with avirulent Pst. In contrast, the pla2α mutant failed to show elevated LPE production in response to Pst-avrRpm1 inoculation (FIG. 2D). The LPE species increased in Pst-avrRpm1-infected wild type plant leaves were LPE16:0, LPE18:1, LPE18:2, LPE18:3, and LPE16:1, as compared to mock-treatment (FIG. 2E). However, only LPE18:1 and LPE16:1 were significantly increased in Pst-avrRpm1-treated leaves and they were detected at low amounts in mock-treated ones (FIG. 2E). LPE18:1 and LPE16:1 are known to be rare lipid species in *Arabidopsis* leaf tissues (Devaiah et al., 2006, *Phytochemistry* 67:1907-1924). Therefore, we examined if these lipid products originate from the membranes of invading bacteria (FIG. 2F). Recombinant PLA$_2$α (rPLA$_2$α) showed antimicrobial activity by attacking bacteria (FIG. 2G). When the Pst-avrRpm1 suspension or the lipid extracts of Pst-avrRpm1 were incubated with rPLA$_2$α protein, LPE18:1, LPE16:0, and LPE16:1 were indeed released from the bacteria or bacterial lipid extracts (FIG. 2F). In order to obtain more direct evidence that some of the LPE species are derived from invading pathogens, Pst-avrRpm1 bacteria were radio-labeled with [$^{14}$C]-ethanolamine and were inoculated into wild type plant leaves. The leaves were harvested 3 h post-inoculation, and the lipid extracts of the infected leaves were separated by TLC. In the control (0 h), which was harvested right after bacterial inoculation, most of the radioactivity was detected in the phosphatidylethanolamine (PE) spot zone but not in the LPE spot zone (0.6%). However, about 9% of the total radioactivity was detected in the LPE spot zone 3 h after bacterial inoculation (FIG. 2H), while less radioactive LPE was found (~3%) in pla2α mutant. These results indicate that some LPEs are generated from the membranes of invading pathogens. We also investigated what kinds of LPE species would be released from the host cells by PLA$_2$α enzymatic activity. When rPLA$_2$α proteins were infiltrated into wild type plant leaves, LPE16:0 and lower amounts of LPE18:1, LPE18:2 and LPE18:3 were detected 3 h post-treatment (FIG. 2F). These results suggest that LPE18:1, a major species of LPE increased in response to Pst-avrRpm1 infection, can also be released from the membranes of host cells. FFAs, which are other lipid products of PLA$_2$α, increased slightly in response to Pst-avrRpm1 inoculation, but increased significantly only following supplementation with rPLA$_2$α. The major FFA species detected were stearic acid (18:0) and palmitic acid (16:0).

Inoculation of wild type leaves with Pst-avrRpm1 increased LPE level by about 35% over the amounts present in mock-treated leaves (FIG. 2C). If we consider that LPE18:1, LPE16:0 and LPE16:1 are newly generated in apoplast, the ~35% increase over total LPE amounts, including the amounts of homeostatic/cytosolic LPE16:0, LPE18:2, and LPE18:3, may represent a significant increase in LPE levels in the apoplast, where LPE is initially compartmented. Even when pla2α mutant plant leaves were infiltrated with rPLA$_2$α 2.5 h after bacterial inoculation, we observed only 100% increase in LPE levels after 30 min in the leaves (FIG. 2D).

Figure 3A:
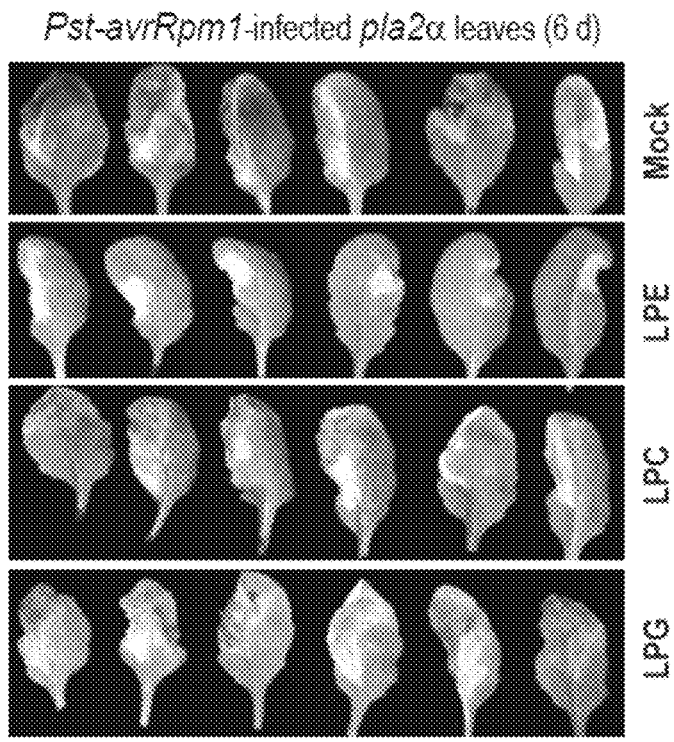
Figure 3B:
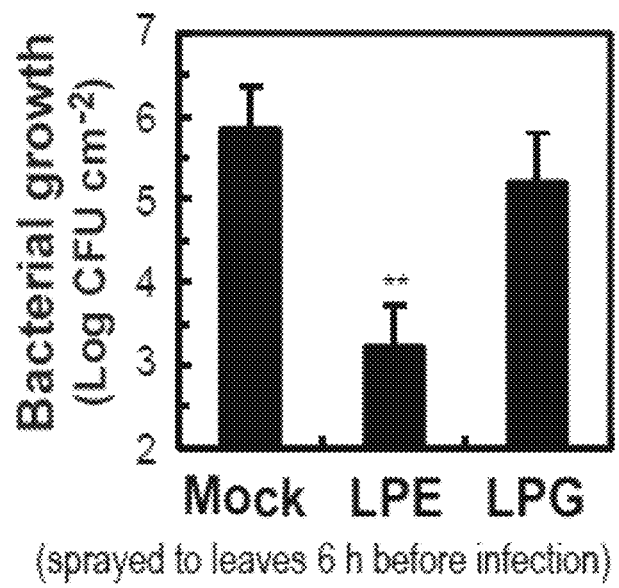
Figures 3C, 3D:
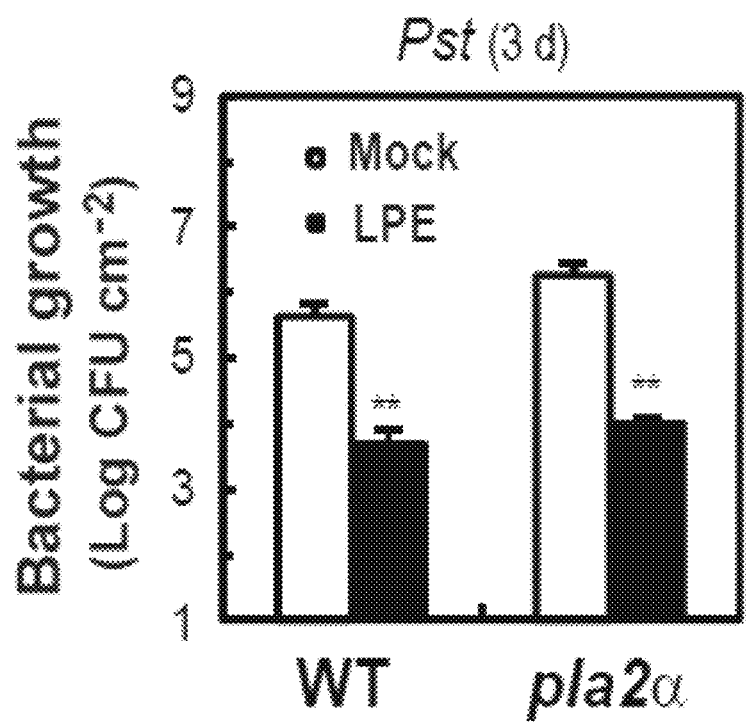
Figure 3E:
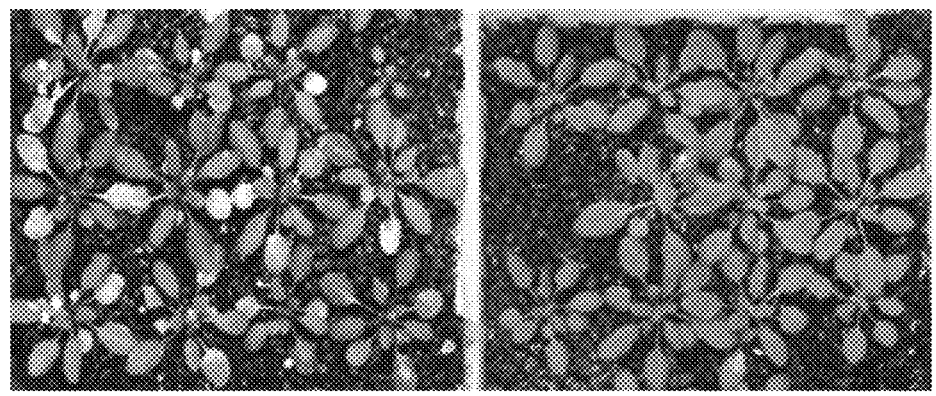
Figure 3F:
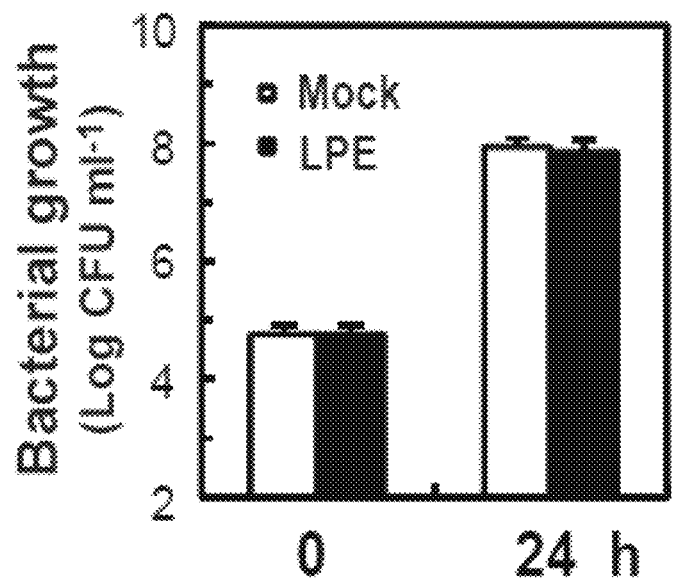

Example 3. Defects of pla2α Mutant in Immune Responses are Restored by Exogenous LPE Based on the analysis of pla2α mutant plants compared to wild type, we hypothesized that the defect in immune responses of the pla2α mutant may be due to the failure to generate the lipid products that mediate downstream immune responses. To test this hypothesis, we supplemented pla2α mutant with LPE18:1 1.5 h after inoculation of Pst-avrRpm1. Indeed, LPE restored the ability of the pla2α mutant to induce local immune responses and restricted the propagation of disease symptoms beyond the HR region (FIGS. 3A and 3B). Very importantly, LPE by itself renders local immunity in the absence of avirulent Pst (FIGS. 3C-3E). LPE induced the expression of the PR genes PR1 and PDF1.2, but not the wound-related genes VSP1 and JMT (FIG. 3C). The acquirement of local immunity by LPE in the absence of bacteria was evidenced by the result that LPE treatment suppressed the bacterial growth of virulent Pst in wild type plants as well as in pla2α mutant plants compared to mock treatment (FIG. 3D). In addition, disease symptoms were much reduced in LPE-sprayed leaves compared to mock-treated ones (FIG. 3E). However, LPE itself had no direct effect on bacterial growth in in vitro assays (FIG. 3F). These results support the hypothesis that the defect of the pla2α mutant is due to the failure to produce lipid mediators such as LPE, which trigger downstream immune responses.

Figure 4A:
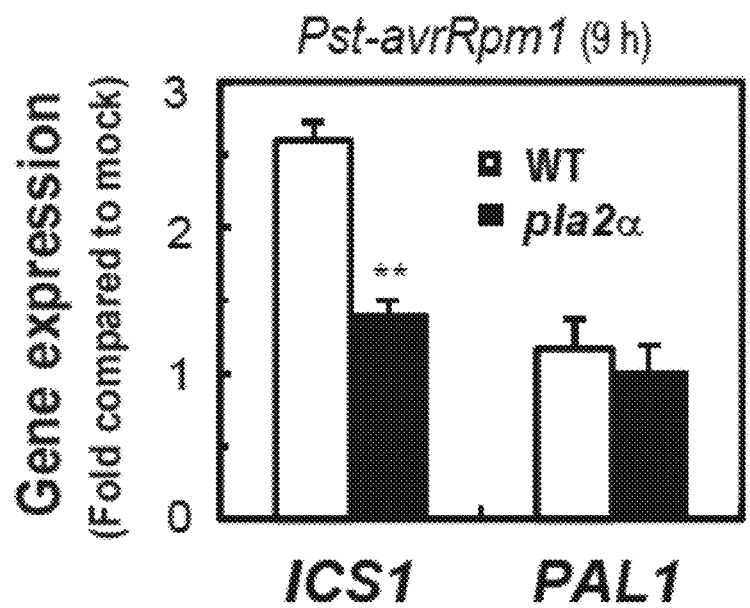
Figure 4B:
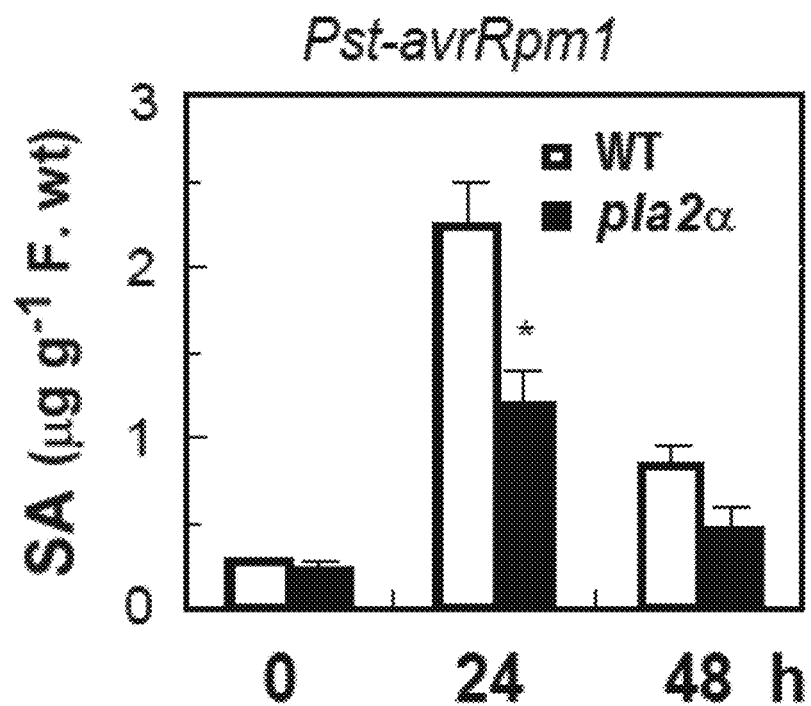
Figure 4C:
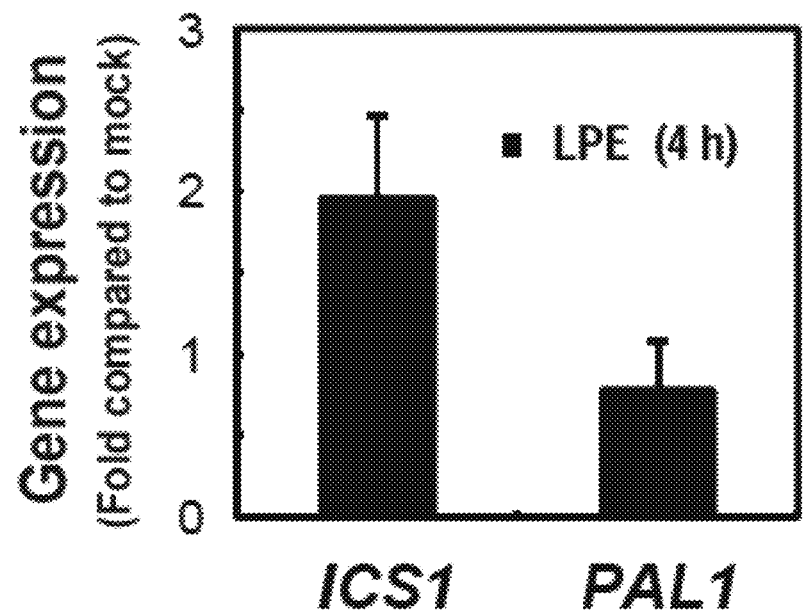
Figure 4D:
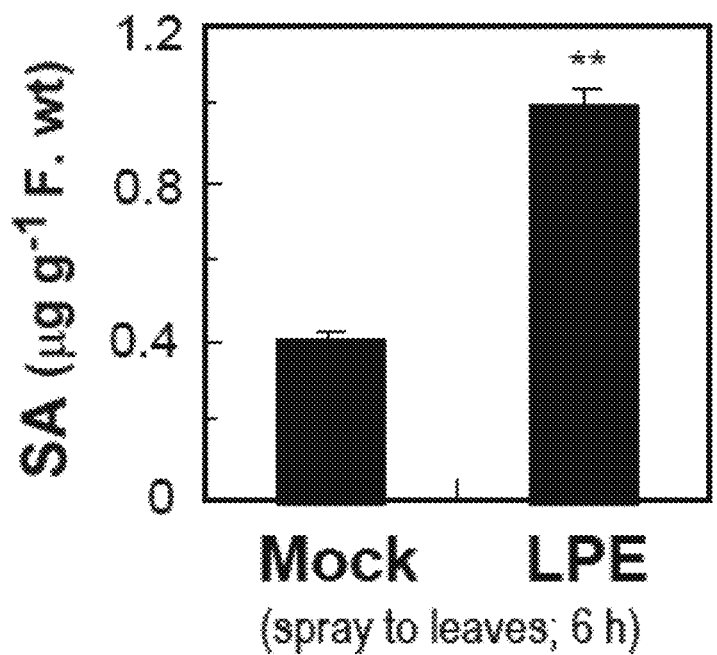

Example 4. ICS1/NPR1-Dependent Salicylic Acid Signaling is Mediated by PLA$_2$α and LPE ICS1 plays a role in host immune responses as a key enzyme in SA biosynthesis. When pla2α mutant plants were inoculated with Pst-avrRpm1, they reduced ICS1 expression by 59% compared to wild type plants (FIG. 4A). In contrast, PAL1 expression in infected pla2α plants was rather increased (FIG. 4A). Moreover, pla2α mutant plants inoculated with Pst-avrRpm1 produced 47% lower levels of free SA than wild type (FIG. 4B). Thus, we hypothesized that pla2α mutant with no generation of lipid products including LPE cannot express ICS1 in response to the challenge of avirulent bacteria, and that this deficit leads to low SA levels, which in turn fail to induce the downstream signaling cascade leading to PR gene expression. To examine this hypothesis, we asked whether exogenous LPE treatment induces ICS1 expression. *Arabidopsis* leaves treated with LPE18:1 displayed ICS1 gene expression 6 h post-treatment (FIG. 4C). In contrast, LPE treatment did not elevate PAL1 expression. ICS1 gene expression was followed by a 2.5-fold increase in SA levels (FIG. 4D). These results suggest that LPE elevates SA levels primarily by inducing ICS1-mediated SA biosynthesis. The ICS1 dependency of LPE signaling was further confirmed by the observations that LPE failed to induce PR1 gene expression in the sid2 mutant plants, as did Pst-avrRpm1 inoculation.

NPR1 is a key regulator of SA-mediated immune responses leading to PR1 gene expression. NPR1 activation requires its translocation from the cytoplasm to the nucleus due to SA-induced redox changes. Since NPR1 activation is mediated by SA, it is conceivable that the LPE-induced increase in SA may activate NPR1. Application of LPE to transgenic plants carrying 35S::NPR1-eGFP indeed activated NPR1 by inducing its translocation from the cytoplasm to the nucleus, as did SA treatment (FIG. 4E). These results support the hypothesis that LPE mediates and/or potentiates R gene-induced SA biosynthesis followed by NPR1 activation and PR1 gene expression.

Figure 5A:
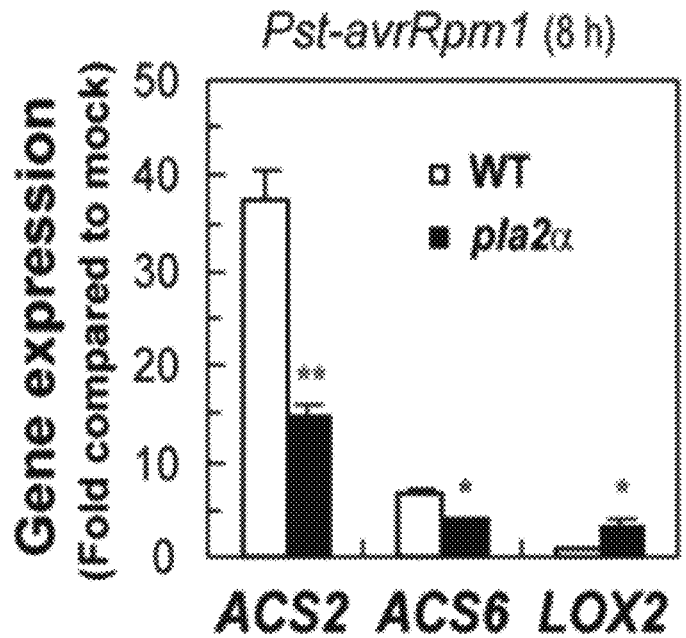
Figure 5B:
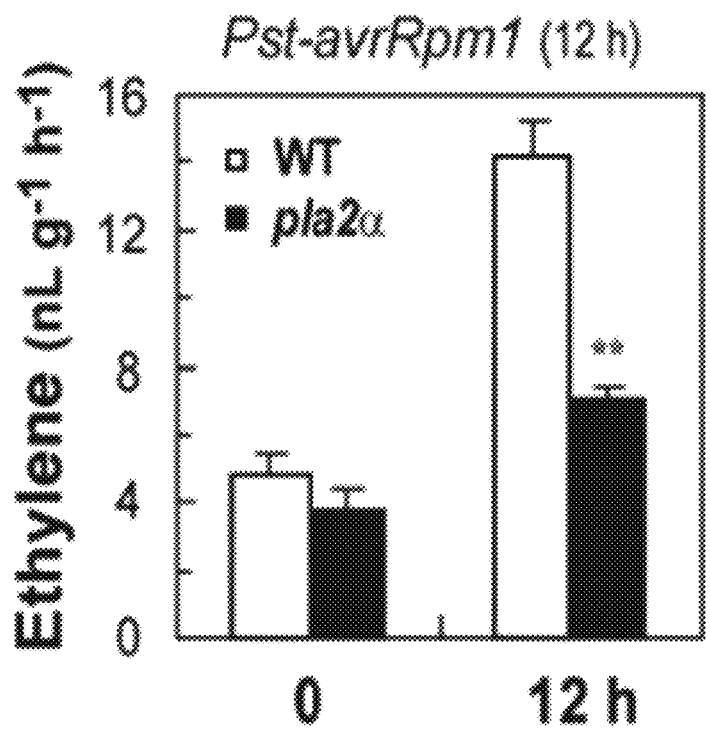
Figure 5C:
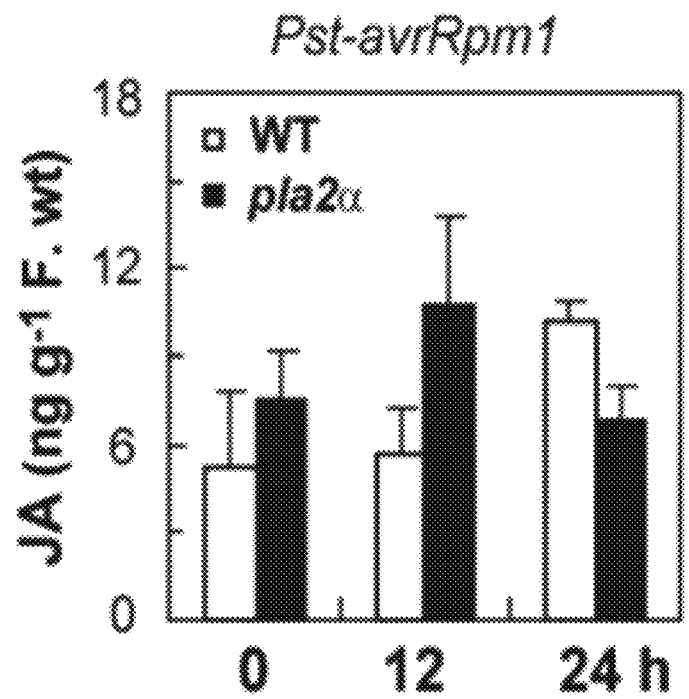
Figure 5D:
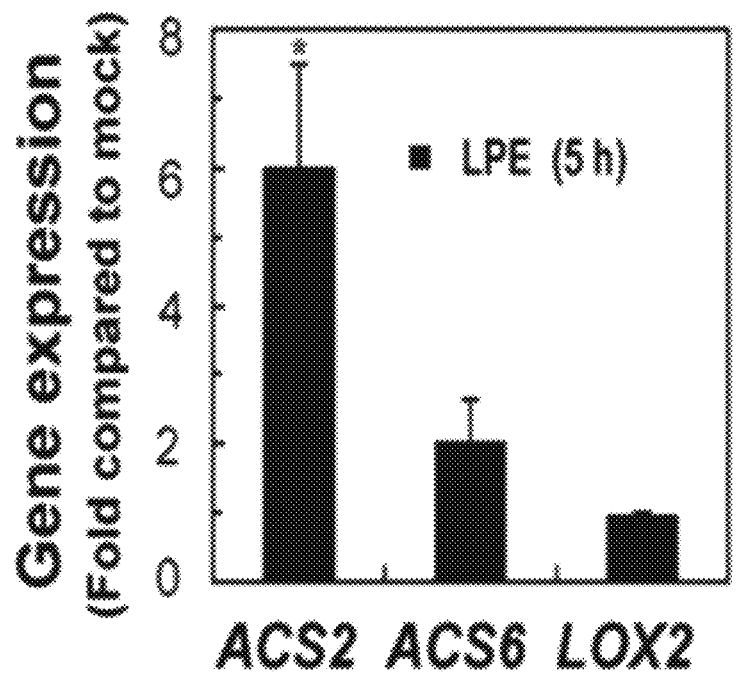
Figure 5E:
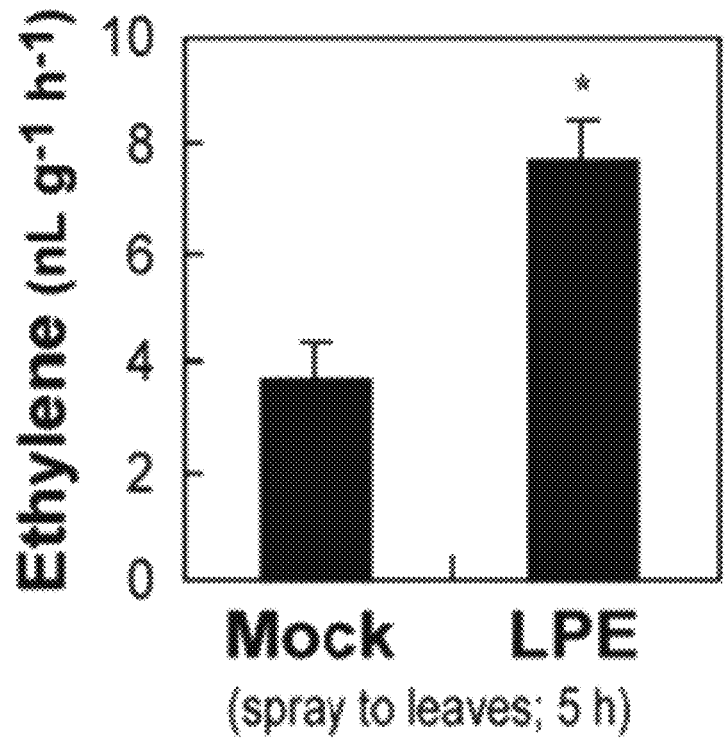
Figure 5F:
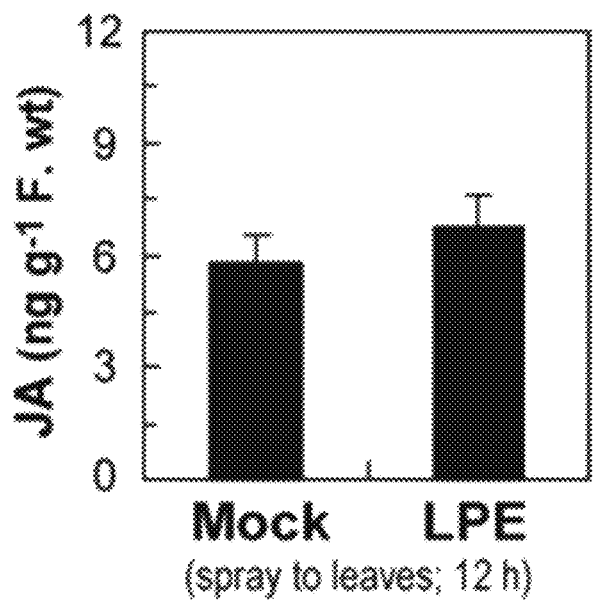

Example 5. Ethylene-Dependent Defense Signaling is Also Mediated by $PLA_2\alpha$ and LPE The pla2α mutant is also defective in PDF1.2 expression in response to inoculation with Pst-avrRpm1 (FIG. 1D), which is known to be mediated by jasmonic acid (JA) and/or ethylene. The pla2α mutant plants have impaired expression of ACC synthase (ACS), ethylene biosynthesis genes, and reduced ethylene production in response to inoculation with Pst-avrRpm1 (FIGS. 5A and 5B). In contrast, the mutant showed unimpaired expression of LOX2 with no significant difference in JA levels as compared to wild type (FIGS. 5A and 5C). *Arabidopsis* leaves treated with LPE exhibited ACS gene expression and an increase in ethylene levels, but did not exhibit a significant increase in LOX2 gene expression or in JA levels (FIGS. 5D-5F). These results suggest that PDF1.2 expression in response to Pst-avrRpm1 infection is ethylene-dependent and is mediated by $PLA_2\alpha$ and its lipid products.

Figure 6A:
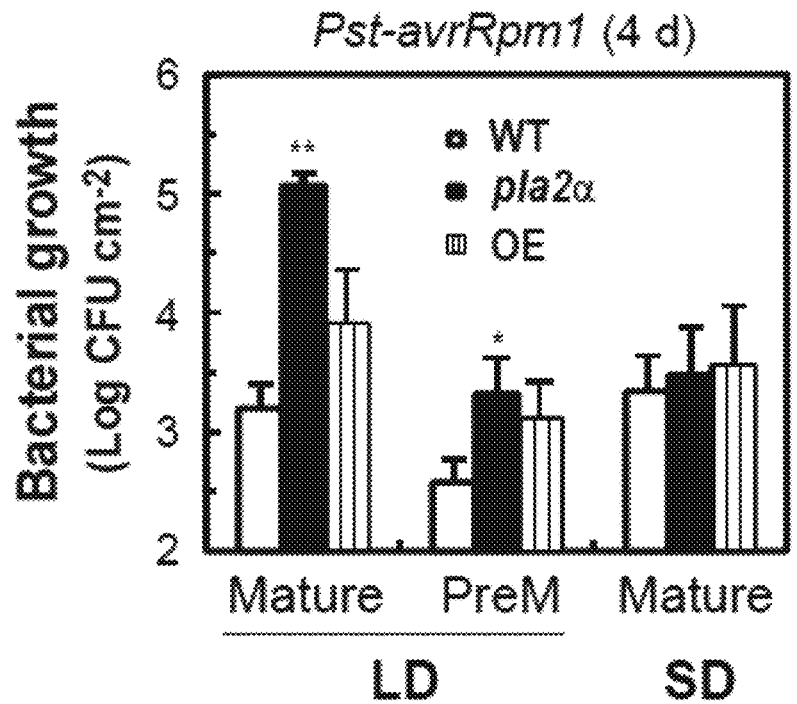
FIGS. 6A to 6F show the result illustrating that a defect in pla2α mutant plant is dependent on leaf growth stage and photoperiod.
Figure 6B:
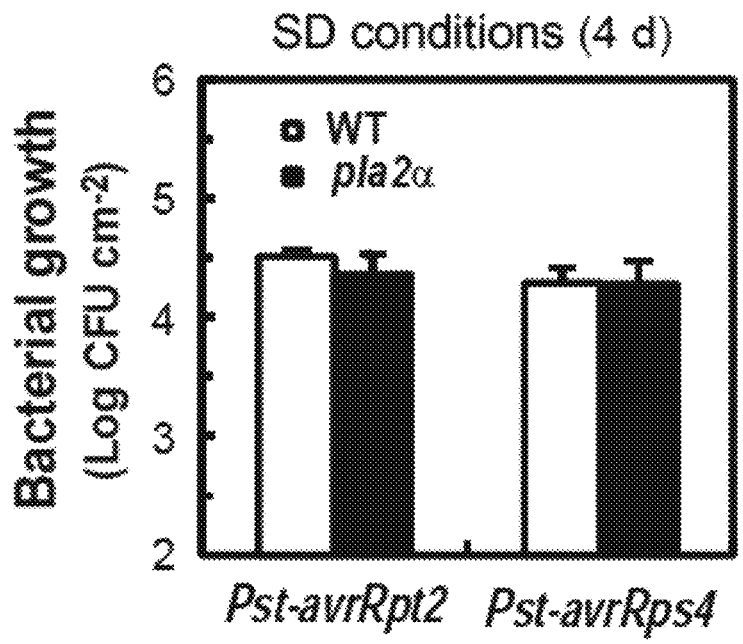
Figure 6C:
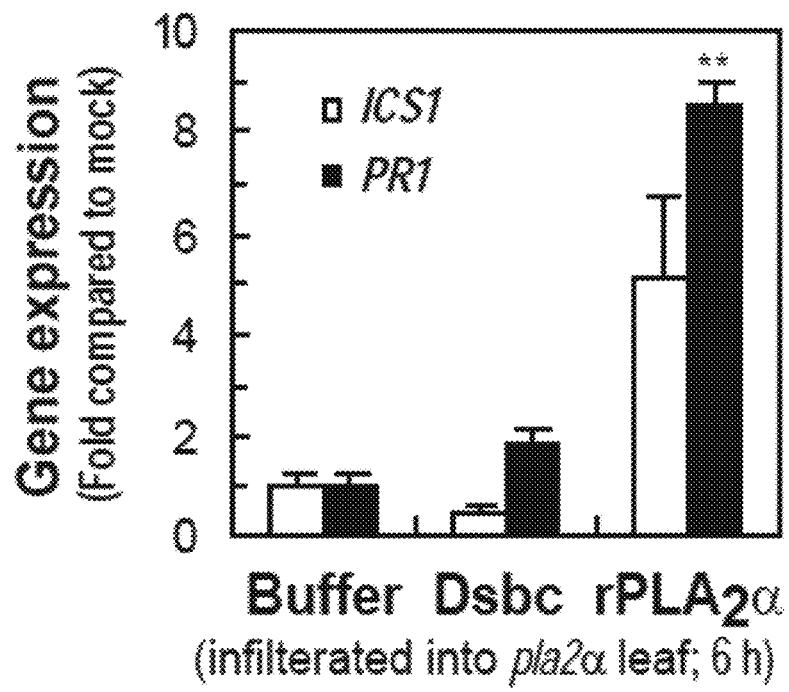
Figure 6D:
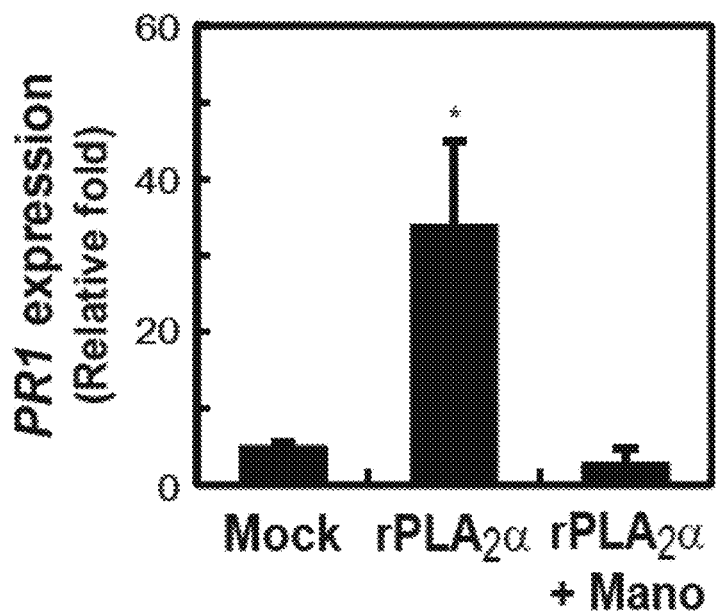
Figure 6E:
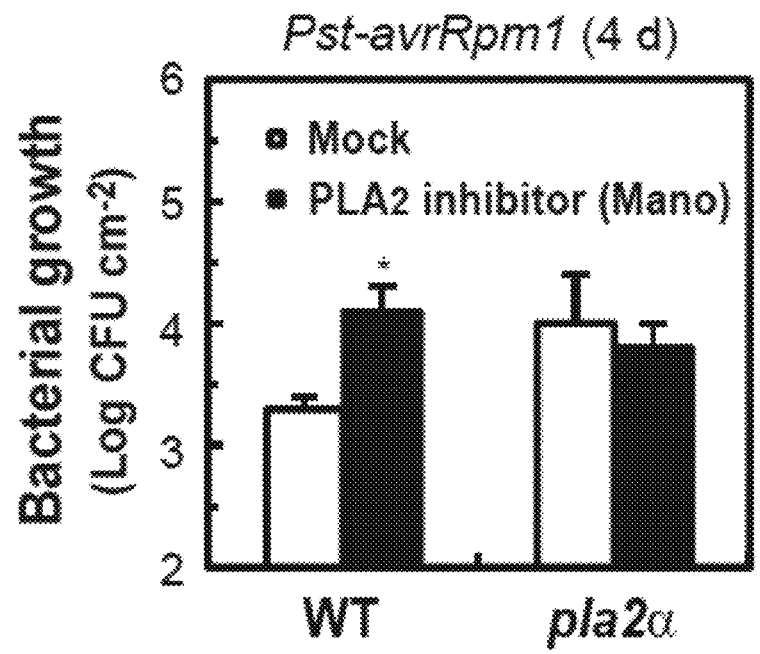
Figure 6F:
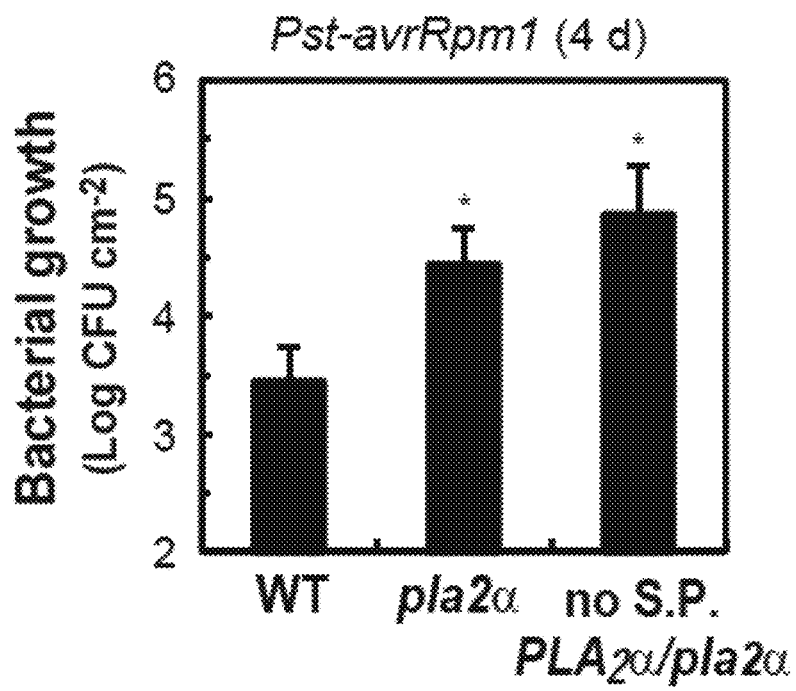

Example 6. Lipid Signal Transduction Mechanism Originating from $PLA_2\alpha$ which Occurs During Plant Immune Response The aforementioned results consistently support the hypothesis that the defects of pla2α mutant plants in local host immune responses under long-day conditions are due to the failure of $PLA_2\alpha$ to generate lipid products such as LPE, which mediate R gene-induced immune response. In support of this hypothesis, exogenous treatment of $rPLA_2\alpha$ proteins to pla2α mutant leaves generated endogenous lipid products including LPE (FIG. 2D) and induced the in situ expression of ICS1 and PR1 genes (FIG. 6C), whereas treatment with $rPLA_2\alpha$ proteins that were catalytically inactivated with a $PLA_2$ inhibitor (manoalide) failed to induce PR1 gene expression (FIG. 6D).

Figure 7:
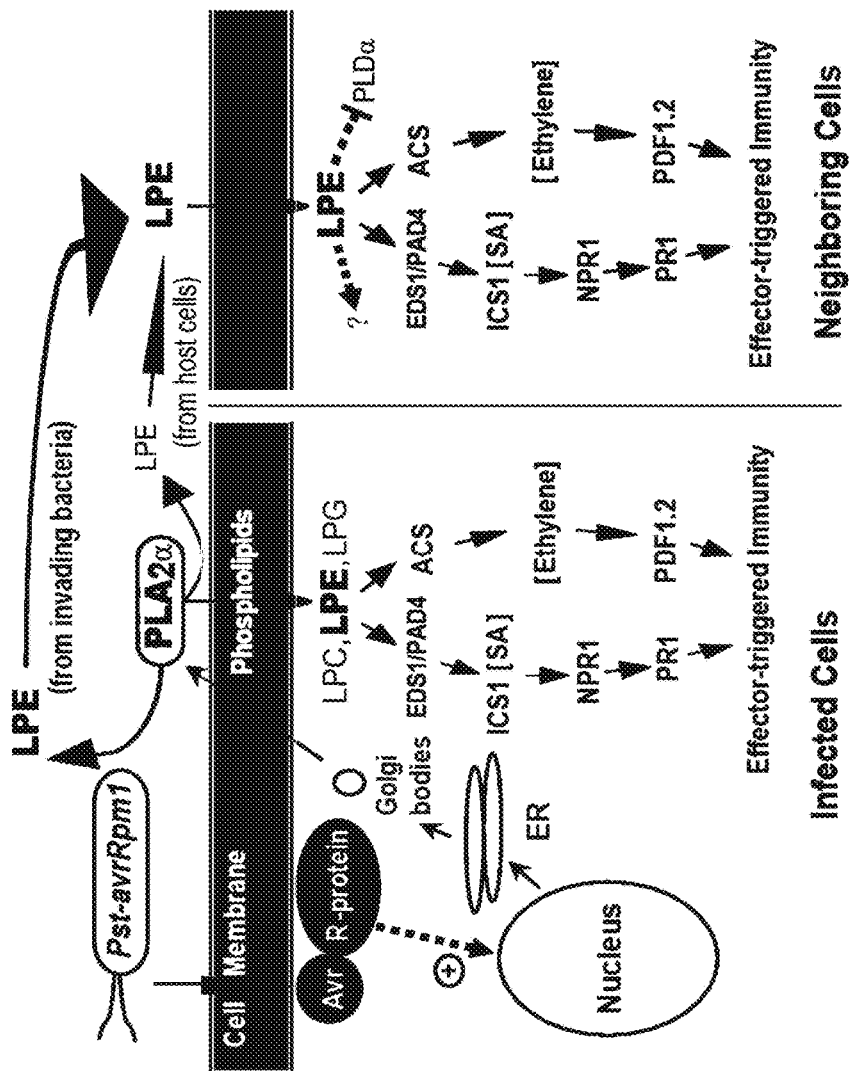
FIG. 7 is a schematic drawing showing the roles played by $PLA_2\alpha$ protein and LPE of the present invention in plant immune response to the bacteria attack.
Figure 8:
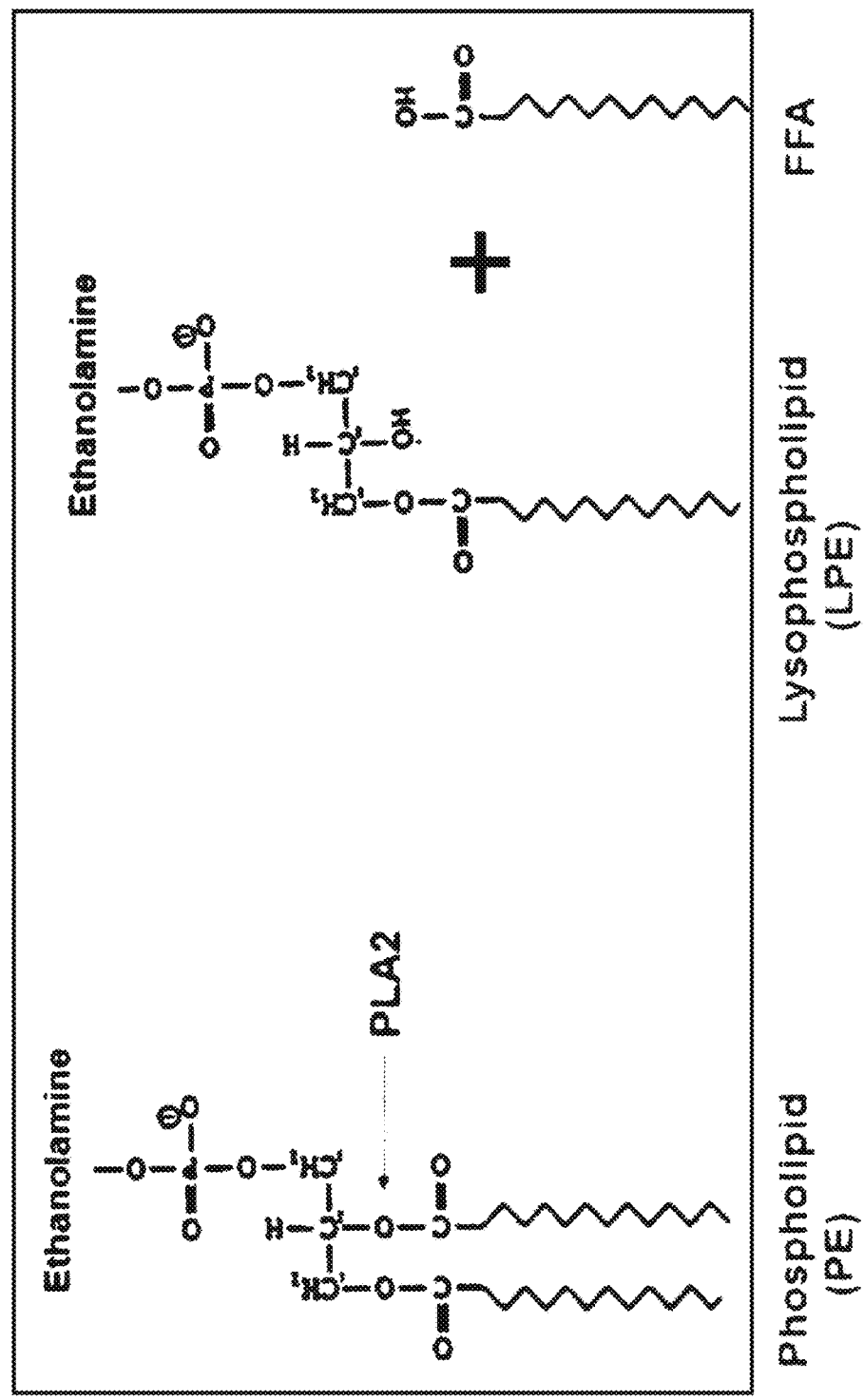
FIG. 8 is a drawing illustrating the principle for producing lysophosphatidylethanolamine (LPE) from phosphatidylethanolamine (PE) when PE as one type of phospholipids is treated with phospholipase $A_2$.

Based on our results, we propose that $PLA_2\alpha$-derived lipid-based signaling operates under long-day conditions as follows. Upon inoculation with avirulent Pst, $PLA_2\alpha$ is rapidly, moderately, and transiently expressed in an R gene-mediated manner. $PLA_2\alpha$ is secreted into the extracellular spaces, where it generates its lipid products including LPE from the membranes of invading bacteria and host cells. The LPE then triggers R gene-induced downstream immune responses through both the ICS1/NPR1-dependent SA signaling leading to PR1 expression and the ACS-dependent ethylene signaling leading to PDF1.2 expression (FIG. 7).

Example 7. Confirmation of Production of LPE18:1 from Lipid Extract of *Pseudomonas*

Figure 9:
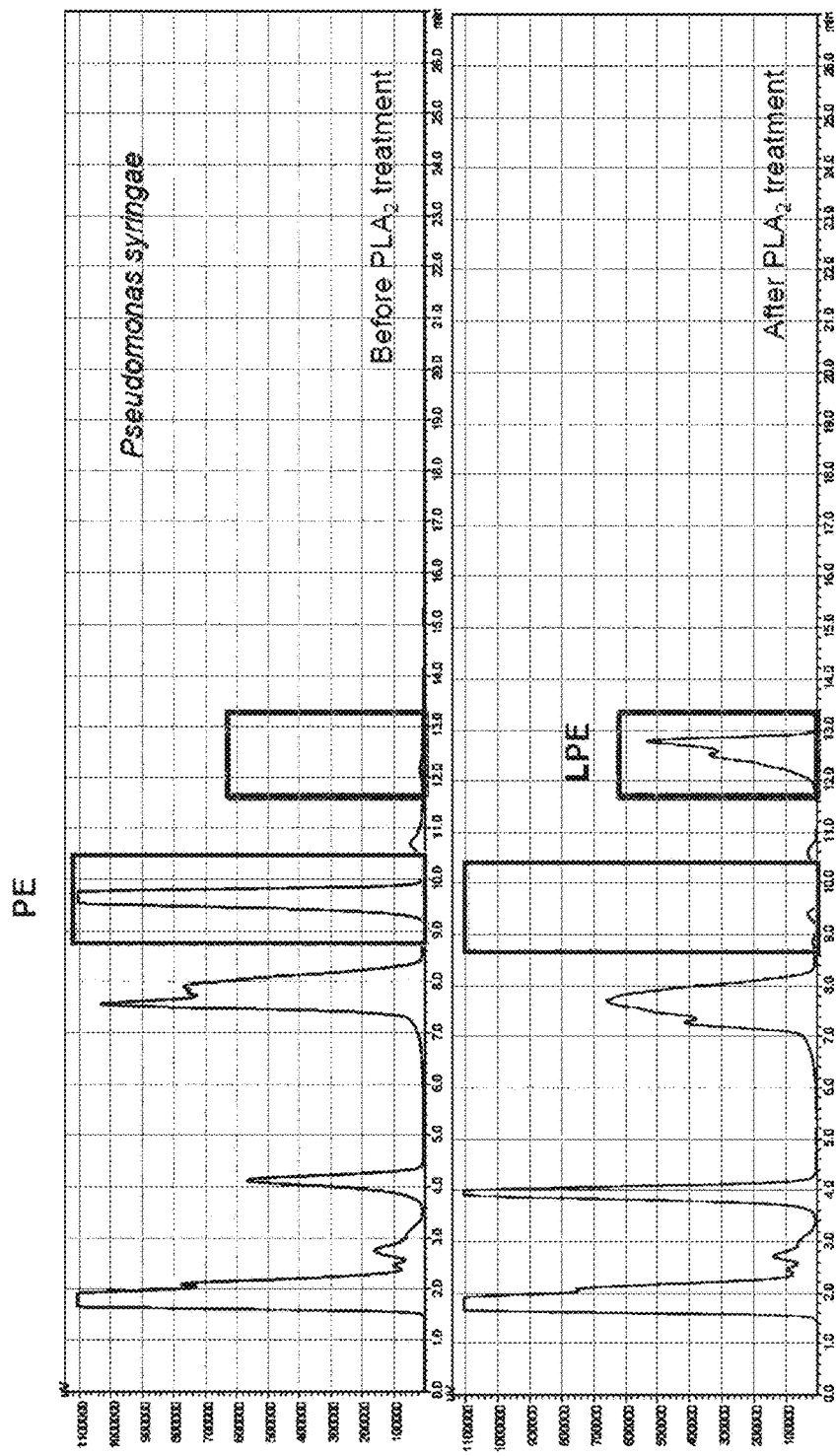
FIG. 9 shows the result of confirming LPE production according to a treatment of the phospholipid extract of Pseudomonas with phospholipase $A_2$. Decomposition of PE and production of LPE before (top) and after (bottom) the treatment of phospholipid extract of Pseudomonas with phospholipase $A_2$ were confirmed by HPLC-ELSD analysis.
Figure 10:
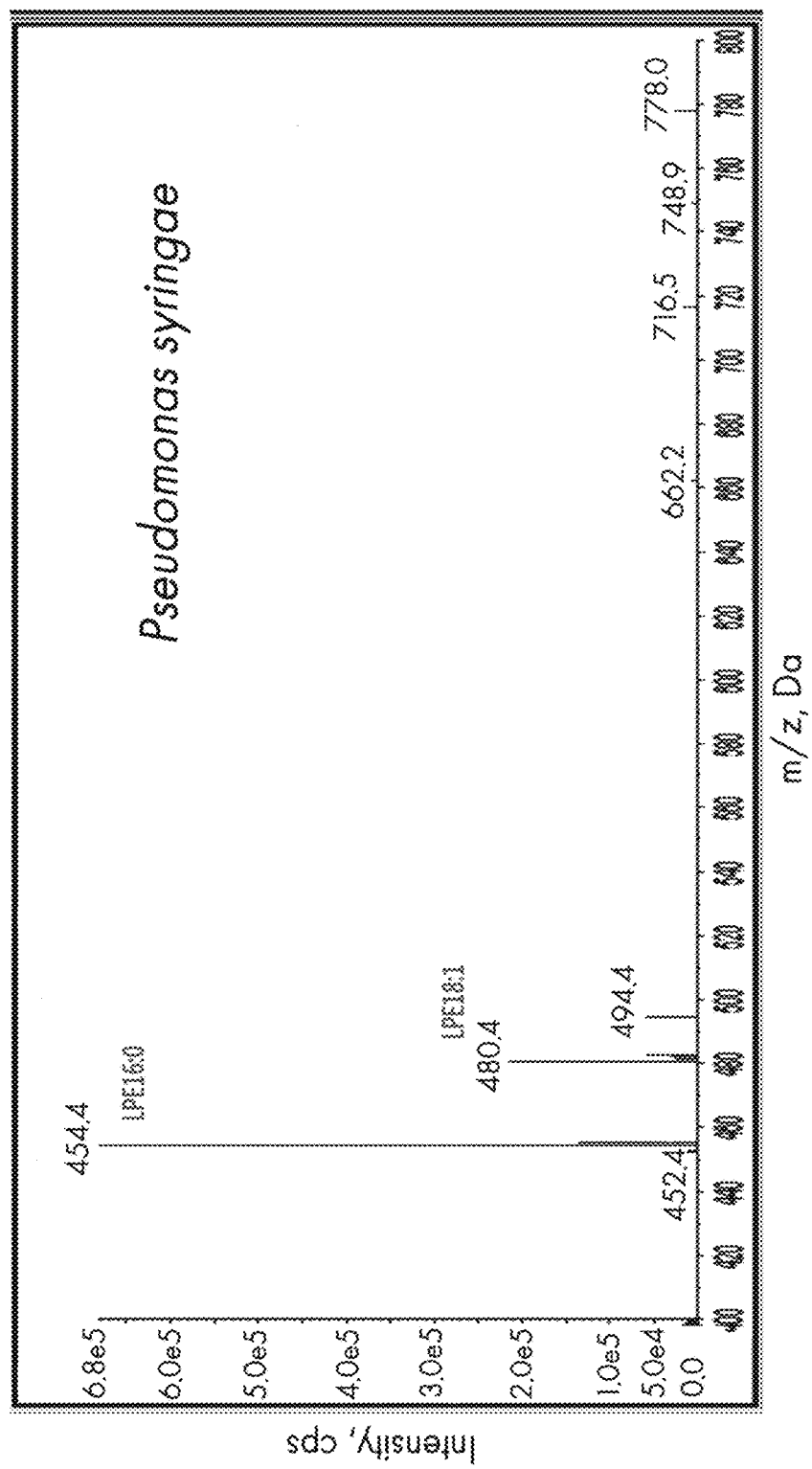
FIG. 10 shows the result of MS/MS analysis illustrating that LPE produced by a treatment of phospholipid extract of Pseudomonas with phospholipase $A_2$ is mainly composed of LPE 16:0 and LPE18:1.

*Pseudomonas syringae* was cultured in a large amount, and, after harvesting, lipids were extracted therefrom. The lipid extract was treated with phospholipase $A_2$, and by using HPLC-ELSD analysis, decomposition of PE (phosphatidylethanolamine) and production of LPE (lysophosphatidylethanolamine) were determined (FIG. 9). According to the result, only the PE peak at the retention time of 9 minutes was shown and the LPE peak at the retention time of 12.5 minutes was weakly shown before the treatment with $PLA_2$ (see, upper chromatogram of FIG. 9). However, after the treatment with $PLA_2$, the PE peak at the retention time of 9 minutes has disappeared while appearance of a new LPE peak at the retention time of 12.5 minutes is marked with a box (see, lower chromatogram of FIG. 9). As such, it was found that the treatment of phospholipids isolated from *Pseudomonas syringae* with phospholipase $A_2$ leads to production of LPE. Based on MS/MS analysis, it was possible to confirm that the main components of the LPE that are produced after treating *Pseudomonas syringae* with $PLA_2$ are LPE18:1 and LPE 16:0 (FIG. 10).

Figure 11:
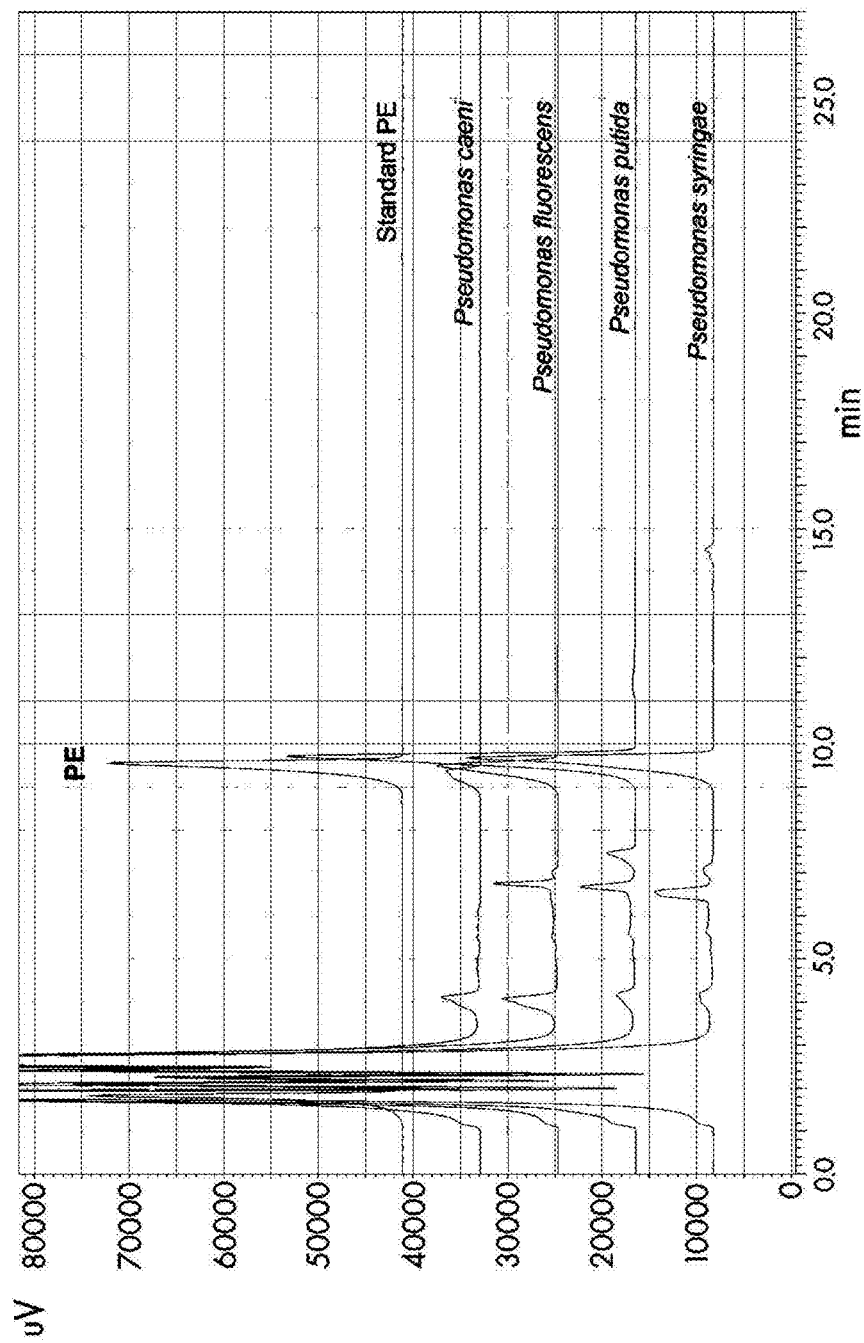
FIG. 11 shows a result of extracting phospholipids to see whether or not PE as an original source material of LPE can be obtained from different types belonging to Pseudomonas sp. other than Pseudomonas syringae, in which phospholipids are extracted from Pseudomonas caeni, Pseudomonas fluorescens, and Pseudomonas putida. As a result, it was found that the phospholipid extracted from other Pseudomonas species is comprised mainly of PE as observed in Pseudomonas syringae.
Figure 12:
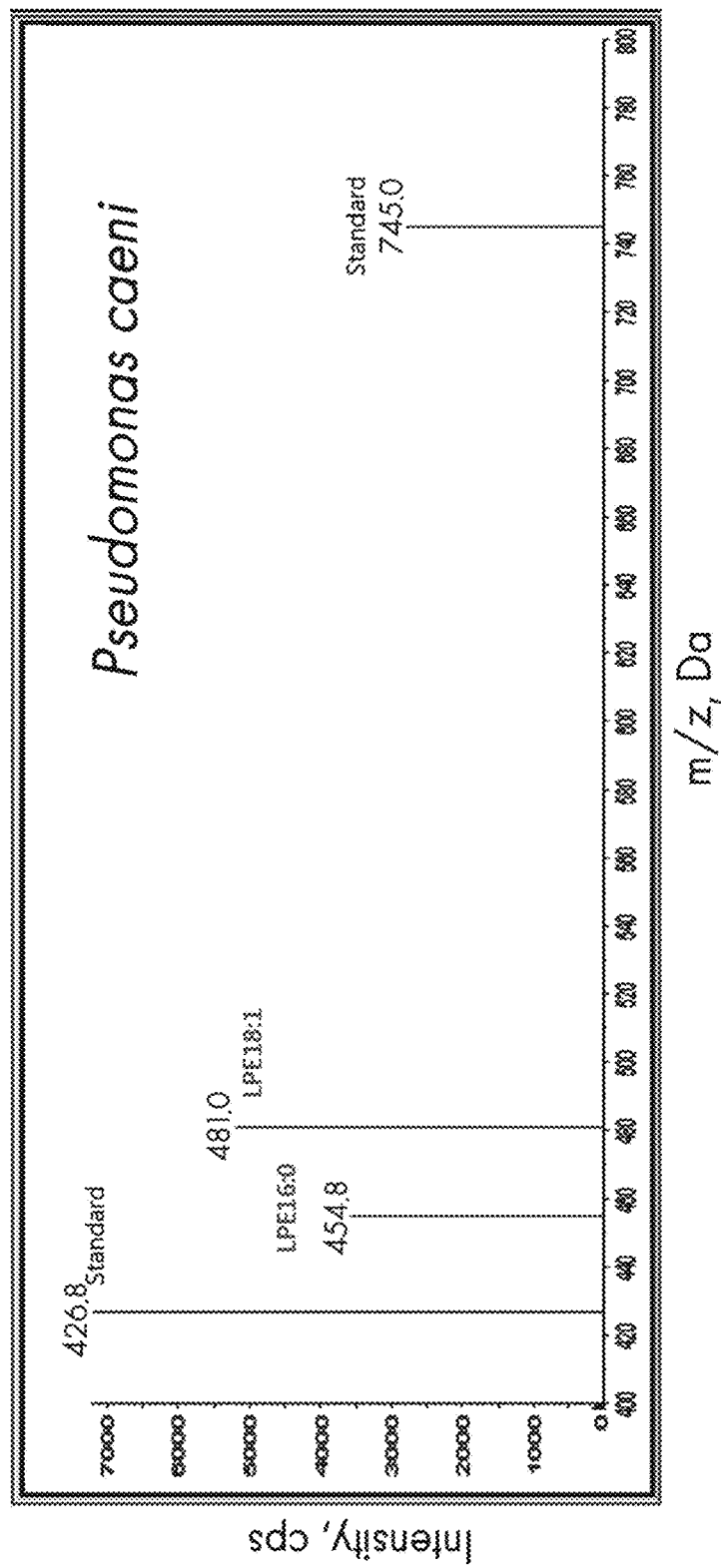
FIG. 12 shows the result of MS/MS analysis illustrating that LPE produced by a treatment of phospholipid extract of Pseudomonas caeni with phospholipase $A_2$ is mainly composed of LPE18:1 and LPE 16:0. The results indicate that content of PE containing the $1^{st}$ acyl chain of 18:1 is quite high in Pseudomonas caeni.
Figure 13:
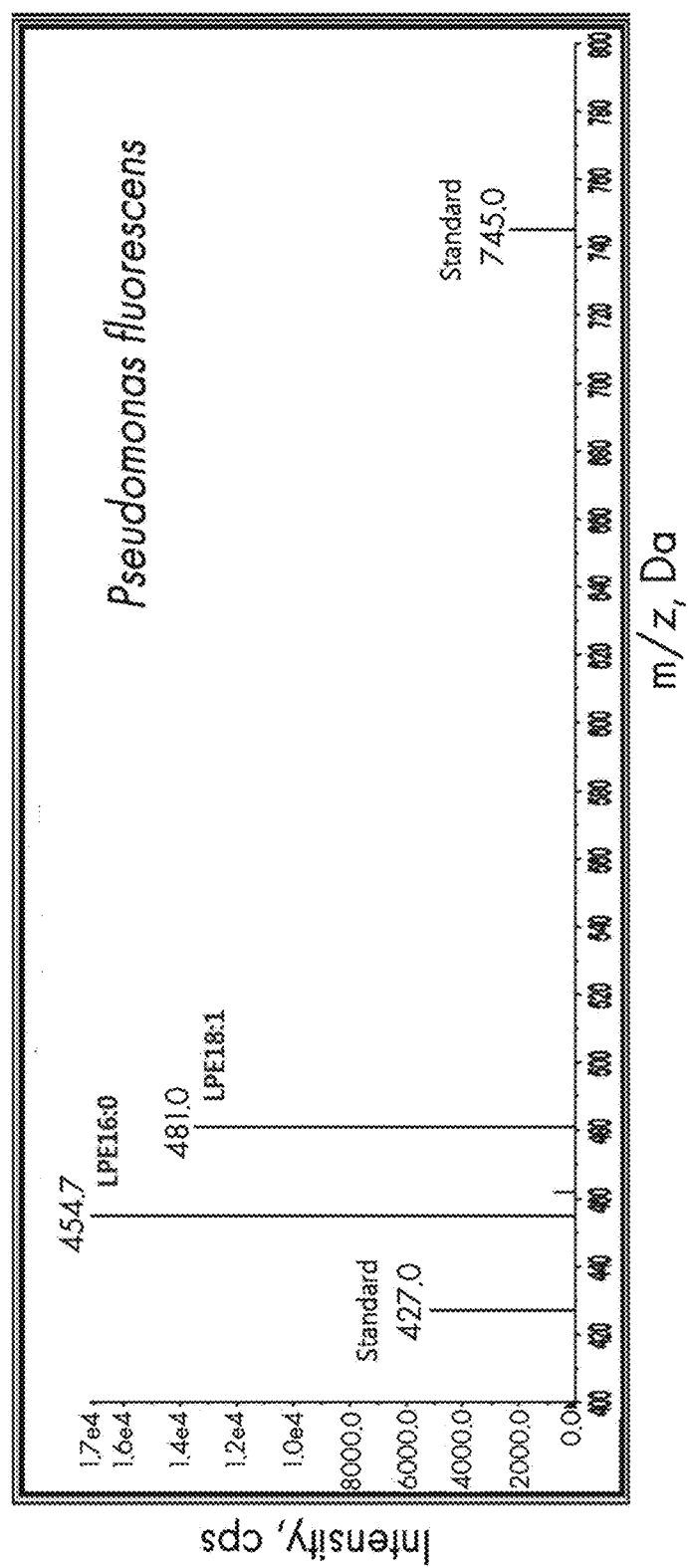
FIG. 13 shows the result of MS/MS analysis illustrating that LPE produced by a treatment of phospholipid extract of Pseudomonas fluorescens with phospholipase $A_2$ is mainly composed of LPE 16:0 and LPE18:1.
Figure 14:
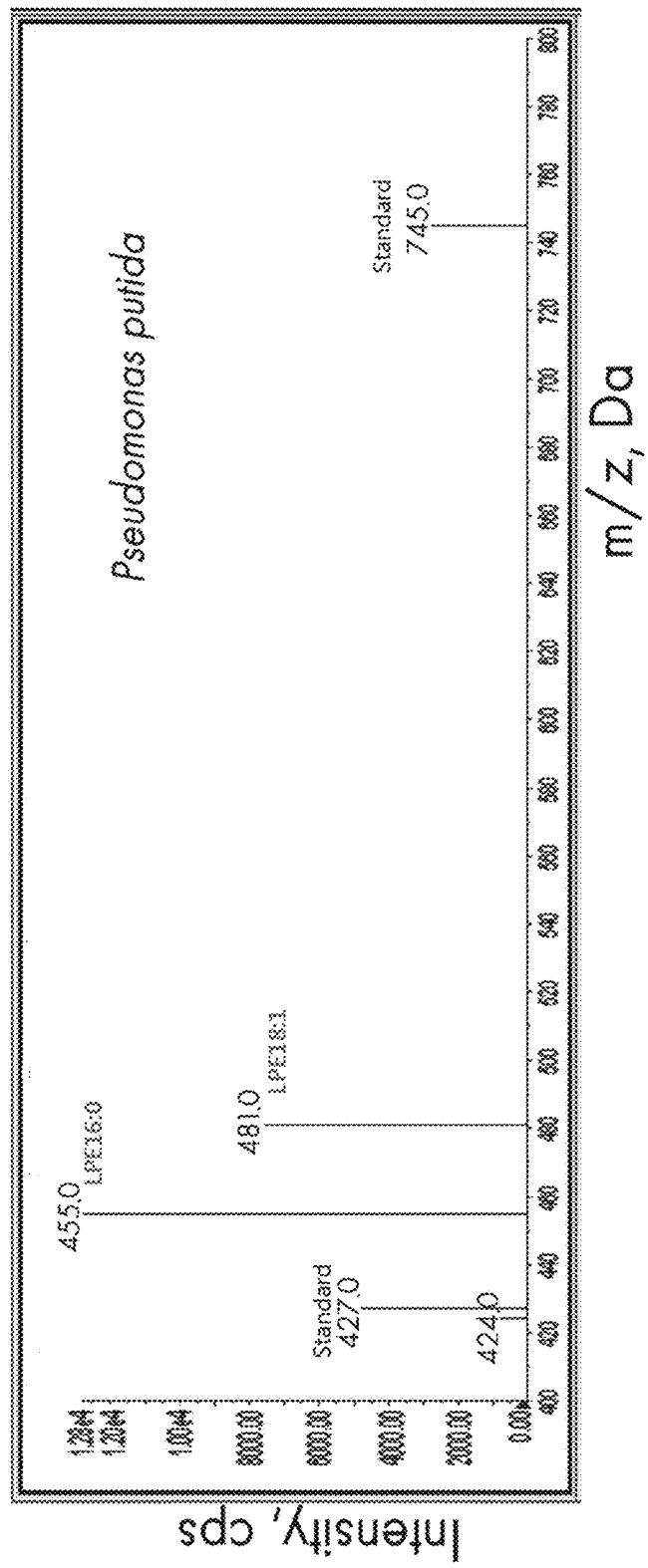
FIG. 14 shows the result of MS/MS analysis illustrating that LPE produced by a treatment of phospholipid extract of Pseudomonas putida with phospholipase $A_2$ is mainly composed of LPE 16:0 and LPE18:1.

Furthermore, in order to see whether or not LPE18:1 can be produced from other microorganisms, phospholipids were extracted from *Pseudomonas caeni, Pseudomonas fluorescens, Pseudomonas putida*, and *Pseudomonas syringae*. As a result, it was found that the content of PE as a raw material source of LPE18:1 is very high in all types of the *Pseudomonas* that are tested (FIG. 11), and LPE18:1 is produced in a large amount in accordance with a treatment with $PLA_2$ enzyme (FIG. 12 to FIG. 14).

Example 8. Determination of Possibility of Producing PE in Microorganisms Other than *Pseudomonas*

Figure 15:
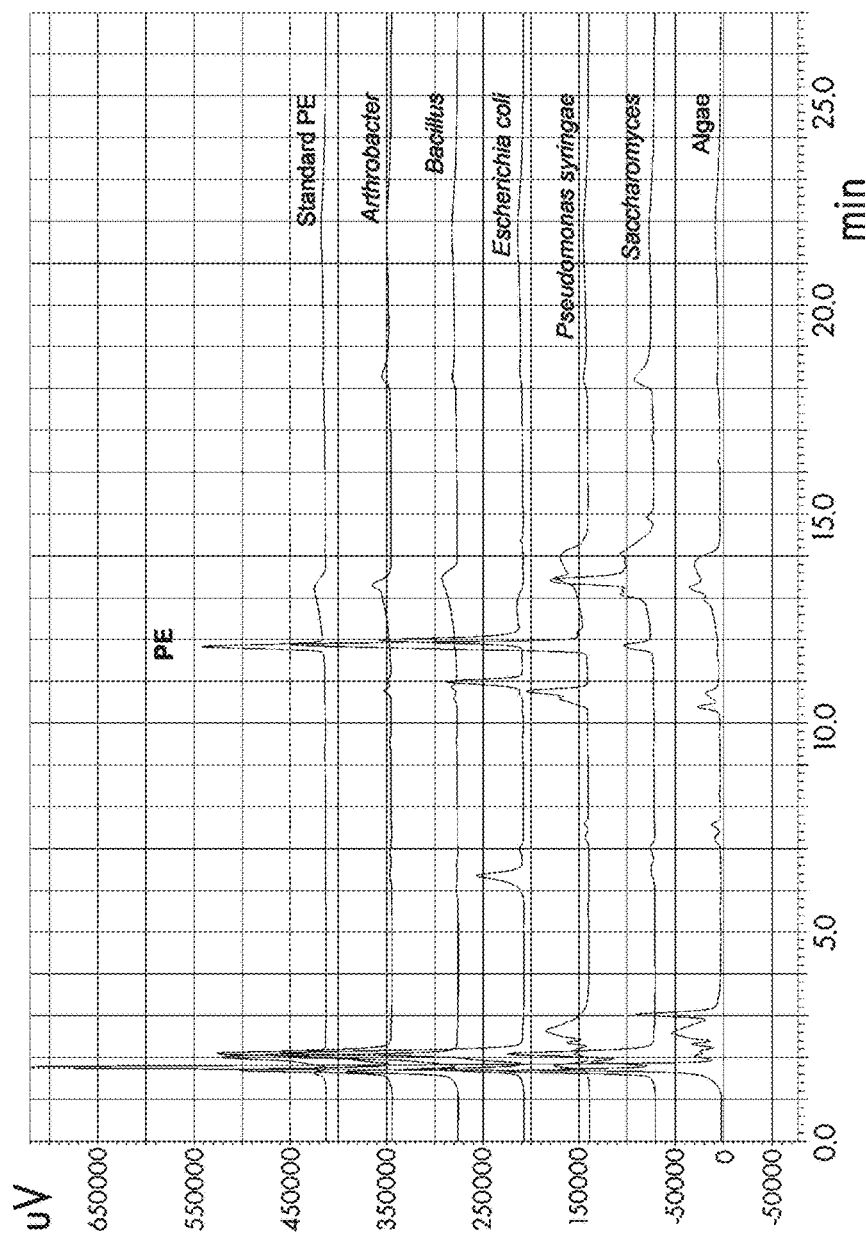
FIG. 15 shows a result of extracting phospholipids to see whether or not PE as an original source material of LPE18:1 can be obtained from a microorganism other than Pseudomonas, in which phospholipids are extracted from Bacillus subtilis and Arthrobacter citres as Gram positive bacteria, Escherichia coli as Gram negative bacteria, Saccharomyces cerevisiae as yeast, and Chlorella vulgaris as algae. As a result, compared to Pseudomonas syringae, PE was detected at a certain level from Escherichia coli but at very low levels in other microorganisms.
Figure 16:
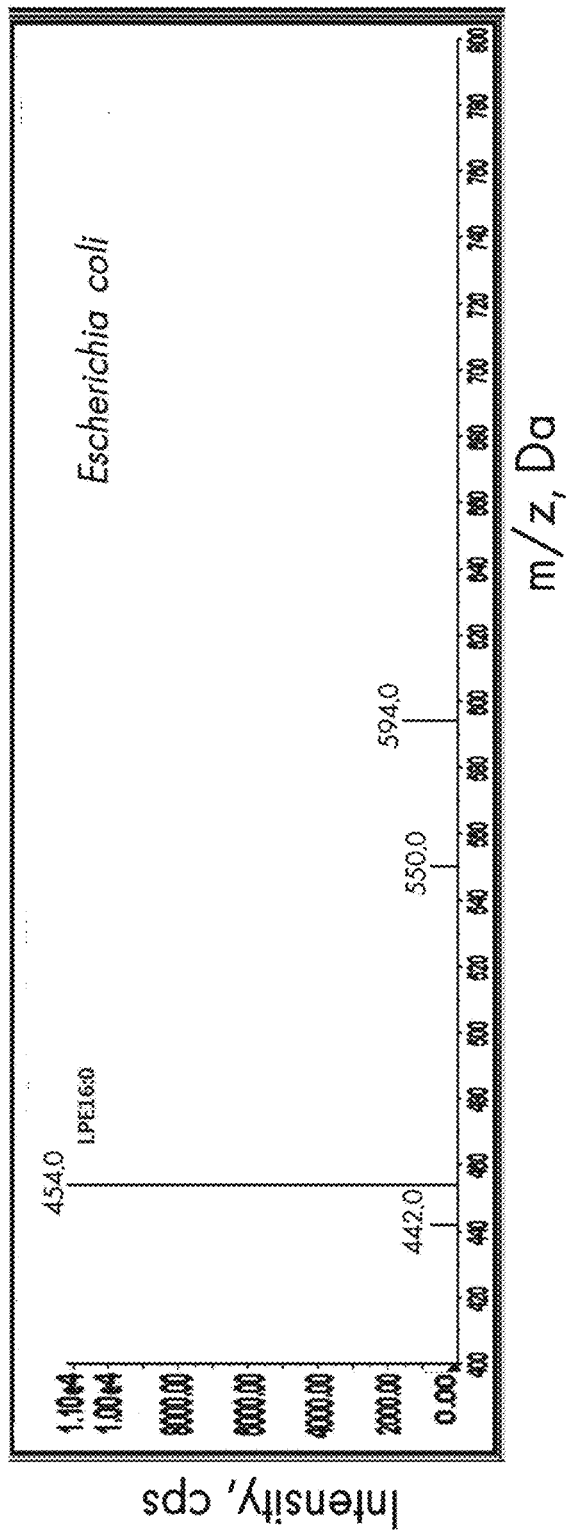
FIG. 16 shows the result of MS/MS analysis illustrating that LPE produced by a treatment of phospholipid extract of Escherichia coli with phospholipase $A_2$ is mainly composed of LPE 16:0 without any LPE18:1.

In order to see whether or not LPE18:1 can be produced from microorganisms other than *Pseudomonas*, phospholipids were isolated from *Escherichia coli* as Gram negative bacteria, *Bacillus subtilis* and *Arthrobacter citres* as Gram positive bacteria, *Saccharomyces cerevisiae* as yeast, and *Chlorella vulgaris* as algae. As a result of the analysis of phospholipids, it was found that PE as a raw material source of LPE is hardly detected from the microorganisms other than *Pseudomonas* (FIG. 15). Although a certain amount of PE has been extracted from *Escherichia coli*, it was found that only LPE 16:0 is produced as a result of treatment with $PLA_2$ (FIG. 16). As such, it was recognized that, from the microorganisms other than *Pseudomonas*, or at least from the microorganisms that are tested, it is difficult to obtain PE capable of producing LPE18:1.

What is claimed is:

1. A method for production of lysophosphatidylethanolamine comprising:
   performing culture of a microorganism of *Pseudomonas* sp.;
   obtaining the microorganism from the culture;
   extracting phospholipid comprising phosphatidylethanolamine from the obtained microorganism;
   treating the extracted phospholipid comprising the phosphatidylethanolamine with phospholipase $A_2$ to produce lysophosphatidylethanolamine; and
   separating and purifying the produced lysophosphatidylethanolamine.

2. The method of claim 1, wherein the lysophosphatidylethanolamine has lysophosphatidylethanolamine 18:1.

3. The method of claim 1, wherein the microorganism of *Pseudomonas* sp. is *Pseudomonas caeni, Pseudomonas fluorescens, Pseudomonas putida*, or *Pseudomonas syringae*.

4. The method of claim 1, wherein the phospholipid is the phosphatidylethanolamine.

5. The method of claim 4, wherein the phosphatidylethanolamine has an 18:1 acyl chain at the first position.

6. The method of claim 1, wherein the phospholipase $A_2$ originates from an animal, a microorganism, or a plant.

* * * * *